(12) United States Patent
Seul

(10) Patent No.: US 7,202,038 B2
(45) Date of Patent: Apr. 10, 2007

(54) TANDEM REPEAT DETERMINATION BY CONCURRENT ANALYSIS OF MULTIPLE TANDEM DUPLEX CONFIGURATIONS

(75) Inventor: Michael Seul, Fanwood, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 350 days.

(21) Appl. No.: 10/913,987

(22) Filed: Aug. 6, 2004

(65) Prior Publication Data

US 2005/0032106 A1    Feb. 10, 2005

Related U.S. Application Data

(60) Provisional application No. 60/492,859, filed on Aug. 6, 2003.

(51) Int. Cl.
*C12Q 1/68* (2006.01)
(52) U.S. Cl. .......................................................... 435/6
(58) Field of Classification Search ..................... None
See application file for complete search history.

(56) References Cited

OTHER PUBLICATIONS

PCT/US04/25330 International Search Report.*
Hizume, et al. "Tandem repeat DNA localizing on the proximal DAPI bands of chromosomes in *Larix*, pinaceae". Genome. vol. 45: 777-783 (2002).

* cited by examiner

*Primary Examiner*—James Martinell
(74) *Attorney, Agent, or Firm*—Eric P. Mirabel

(57) ABSTRACT

Disclosed is a method of analyzing tandem repeats using one or more probes, each such probe may lack an anchoring sequence but contains one or more tandem repeat sequences complementary to the target tandem repeat sequences. In one embodiment, each probe is attached, via its 5' end, to an encoded microparticle ("bead"), wherein the code—implemented by way of a color scheme—identifies the sequence and length of the probe attached thereto. Also disclosed are methods relating to the analysis of partial duplex configurations involving only partial overlap between probe and target repeats and thus "overhangs" of probe repeats on the 3' and/or 5' ends of the target repeats.

20 Claims, 22 Drawing Sheets

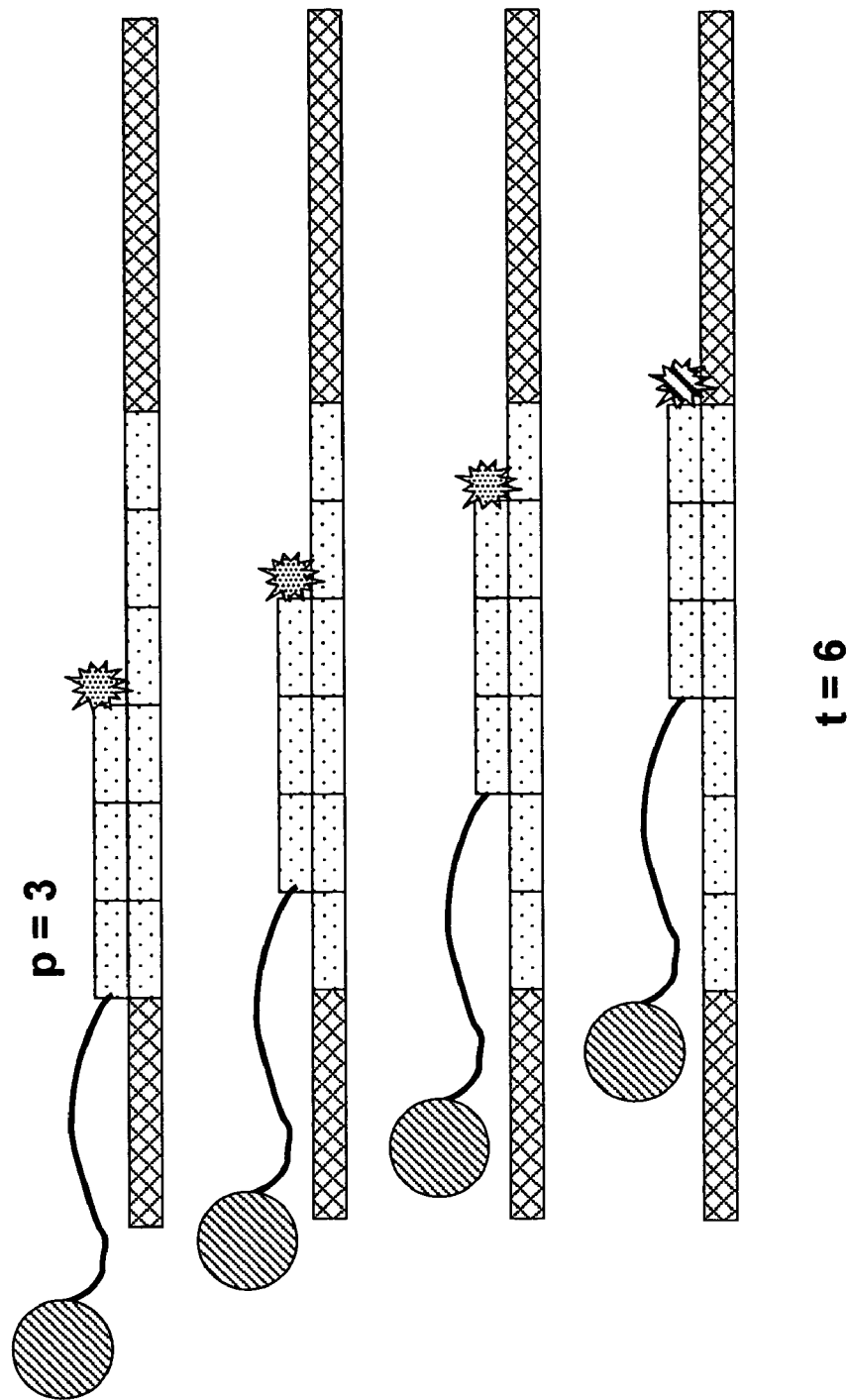

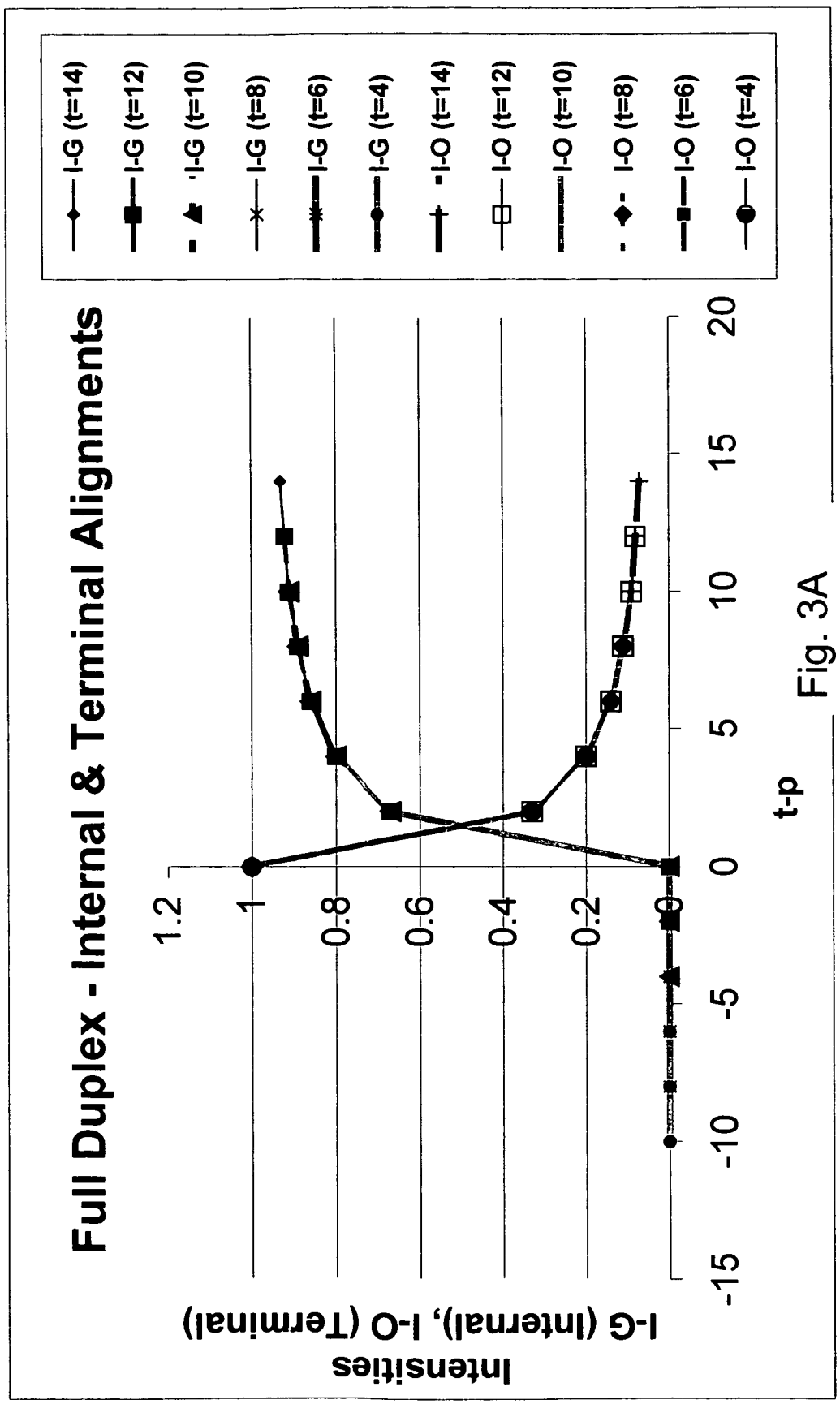

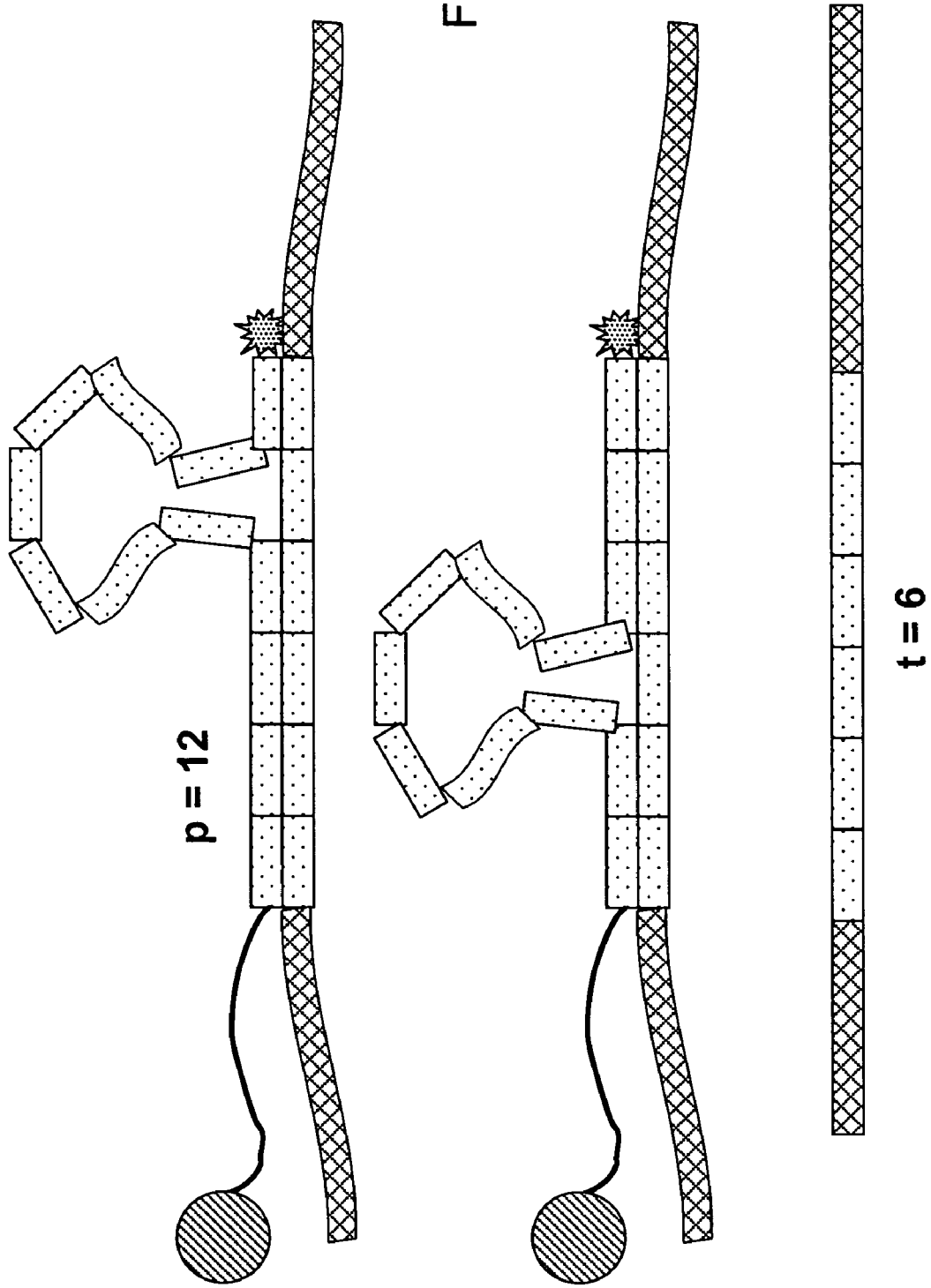

SEQUENCE LISTING

```
<160> NUMBER OF SEQ ID NOS: 4

<210> SEQ ID NO 1
<211> LENGTH: 7
<212> TYPE: DNA
<213> ORGANISM: Artificial Sequence
<220> FEATURE:
<223> OTHER INFORMATION: artificial primer

<400> SEQUENCE: 1 caccatg                                                              7

<210> SEQ ID NO 2
<211> LENGTH: 5
<212> TYPE: DNA
<213> ORGANISM: Artificial Sequence
<220> FEATURE:
<223> OTHER INFORMATION: artificial primer

<400> SEQUENCE: 2 aagta                                                                5

<210> SEQ ID NO 3
<211> LENGTH: 4
<212> TYPE: DNA
<213> ORGANISM: Artificial Sequence
<220> FEATURE:
<223> OTHER INFORMATION: artifidal primer

<400> SEQUENCE: 3 catt                                                                 4

<210> SEQ ID NO 4
<211> LENGTH: 5
<212> TYPE: DNA
<213> ORGANISM: Artificial Sequence
<220> FEATURE:
<223> OTHER INFORMATION: artificial primer

<400> SEQUENCE: 4 aagtg                                                                5
```

TANDEM REPEAT DETERMINATION BY CONCURRENT ANALYSIS OF MULTIPLE TANDEM DUPLEX CONFIGURATIONS

RELATED APPLICATIONS

This application claims priority to U.S. Provisional Application Ser. No. 60/492,859, filed Aug. 6, 2003.

BACKGROUND

The analysis of polymorphisms in the number of repeated DNA sequence elements ("repeats") in certain designated genetic loci has a variety of applications in molecular diagnostics and biomedical research. These applications include the molecular determination of identity for parentage and forensic analysis, the diagnosis of genetic diseases including Huntington's disease and fragile X syndrome caused by the expansion of trinucleotide repeats, the analysis of genetic markers relating to gene regulation, as in the case of dinucleotide repeat polymorphisms in the transcription region of several cytokines, as well as mapping and linkage analysis.

Variable number tandem repeats ("VNTRs") represent one type of repeat length polymorphism (See Nakamura Y., et al. (1987), Science 235: 1616–1622; U.S. Pat. Nos. 4,963,663; 5,411,859) resulting from the insertion, in tandem, of multiple copies of identical segments of DNA, known as minisatellites, typically 10 bp to 100 bp in length. VNTR markers are highly polymorphic, in fact more so than base substitution polymorphisms, sometimes displaying up to forty or more alleles at a single genetic locus. The determination of the number of repeats in VNTRs would provide a means for identity typing but for the fact that there are few fast and accurate methods for this purpose. The commonly used method involves enzymatic digestion of the VNTR-containing nucleic acid segment, followed by Southern blotting, a labor-intensive and time-consuming procedure. Alternative methods invoking the polymerase chain reaction (PCR) (U.S. Pat. No. 4,683,202) are of limited utility in the analysis of VNTRs because of PCR's shortcomings in reliably amplifying segments exceeding 3,000 bases in length. Only a few amplifiable VNTRs have been developed, making them, as a class, impractical for linkage mapping and identity typing.

More frequent, and more polymorphic than VNTRs are microsatellite loci, consisting of repeating units typically comprising only a few bases. Short tandem repeats ("STRs") represent an example of "microsatellite" markers. As with amplifiable VNTRs, alleles of microsatellite loci differ in length, but in contrast to VNTRs contain, in the case of STRs, only two to seven perfect or imperfect repeated sequence elements displaying two, three, four or rarely five bases. Available amplification protocols produce small products, generally from 60 to 400 base pairs in length, permitting the determination of STR repeat numbers by means of amplification followed by gel analysis. Care must be taken in selecting PCR primers in order to eliminate amplification products containing alleles of more than one locus.

Hybridization, widely used for the analysis of polymorphisms generally, also has been used for the analysis of variations in the number of repeats. Hybridization-mediated analysis of point mutations—i.e., base substitution—as well as deletions and insertions, typically involves a pair of allele specific oligonucleotides (ASOs) of which one is designed to be complementary to the normal ("wild type"), and the other is designed to be complementary to the variant ("mutant") sequence. However, in "multiplexed" configurations, calling for the concurrent analysis of multiple polymorphisms, cross-hybridization often limits the reliability of the analysis.

One hybridization-mediated method of analyzing variations in the number of repeats requires a large number of allele-specific oligonucleotides, each such ASO matching in length one of the alleles. For example, U.S. Pat. No. 6,307,039 discloses a method wherein ASOs are provided so as to permit template-mediated probe extension if, and only if the number of repeats in the probe sequence is equal to or less than the number of repeats in the target sequence. Using a set of such ASO probes, the set containing at least one probe for each anticipated configuration of target repeats, the number of target repeats can be determined by monitoring the outcome of the extension reaction for all probes so as to identify that probe in the set whose repeat count matches that of the target.

This approach has several disadvantages which seriously impair its practical utility. First, in order to eliminate errors in the measurement of repeat length due to "slippage", that is, shifts in probe-target alignment, probes must contain an "anchoring" sequence of sufficient length to ensure predictable alignment with the flanking sequence located upstream from the target repeat. Second, target and probes of increasing lengths form duplexes which contain increasing numbers of repeats and thus display widely varying thermodynamic stabilities, a feature which renders an isothermal assay protocol impractical and instead requires careful real-time temperature control. Third, a probe must be provided for each possible target polymorphism, a requirement that implies large probe sets and complex assay protocols and hence considerable cost. For example, a typical application such as the implementation of a 13-marker STR panel commonly used for forensic analysis, will require of the order of ~100 probes. In cases such as Huntington's disease, characterized by up to forty or more triplet repeats, each in the large set of requisite probes must be precisely aligned with the target by way of a long anchoring sequence, implying an assay design of considerable complexity. Finally, this approach does not accommodate cases involving polymorphisms with an unknown range of repeats such as the FGA marker commonly employed for parentage analysis.

A method of concurrent analysis of multiple tandem repeats, invoking an array of a minimal number of probes, regardless of the possible number, known or unknown, of target repeats, while simplifying the assay design, for example by eliminating the requirement for an anchoring sequence, clearly would be desirable.

SUMMARY

Described is a method of analyzing tandem repeats using one or more probes, each such probe may lack an anchoring sequence but contains one or more tandem repeat sequences complementary to the target tandem repeat sequences. In one embodiment, each probe is attached, via its 5' end, to an encoded microparticle ("bead"), wherein the code—implemented by way of a color scheme, as shown in FIG. 1—identifies the sequence and length of the probe attached thereto.

If the number of repeat sequences in the probe is p, and the number of repeat sequences in the target is t, then, provided that p is less than t (p<t), probe and target can hybridize—with equal likelihood—in any of t−p+1 possible (degenerate) configurations differing only in the phase of alignment. These configurations, also referred to herein as full-length duplex repeat configurations or full-length duplex configurations, involve a full overlap of probe repeats with target repeats (t>p) or target repeats with probe repeats (t≦p). For example, the possible full-duplex configurations formed between a probe with three repeats and a target with six repeats are shown in FIG. 2: one unique "terminal alignment" configuration, wherein the probe is aligned with the "5'-terminal" nucleotide in the target repeat, and three of "internal alignment" configurations wherein the probe is aligned with "repeat-internal" nucleotides in the target repeat. Differential labeling of the terminally aligned duplex states and the internally aligned duplex states, for example by way of single base extension using differentially labeled ddNTPs as disclosed herein, permits the "counting" of target repeats using one or more probes containing a known number of probe repeats.

Successive determinations of target repeat numbers may be made by placing probes in solution so as to permit interaction with one target. Preferably, two or more probes designed for the analysis of one target sequence, these probes having different probe repeat numbers, $p1<t$ and $p2<t$, $p1 \neq p2$, or a set of such two or more probes for the analysis of multiple target sequences, are used in a parallel assay format of analysis.

Preferably, the temperature of the assay may be set so that, for each probe containing p (<t) probe repeats, only full-length duplexes, i.e., those containing p duplex repeats, are stable, but duplexes containing fewer than p duplex repeats are not. Alternatively, the assay temperature can be set to ensure stability of a duplex containing at least p−k, $1 \leq k < p$, duplex repeats. Using standard methods of temperature control, the assay also may be performed at several operating temperatures to monitor the evolution of partial and full duplex states of differing thermodynamic stability. In other instances, the temperature may be set to a value exceeding the nominal "melting" temperatures of some or all duplexes, for example when those "melting" temperatures are low compared to the preferred temperature of operation of the polymerase mediating the extension reaction for the labeling of internally and terminally aligned states. This condition generally will favor the formation of partially or completely denatured probe-target duplex states. Also disclosed are weight functions to model these situations.

Also described are methods relating to the analysis of partial duplex configurations involving only partial overlap between probe and target repeats and thus "overhangs" of probe repeats on the 3' and/or 5' ends of the target repeats. The formation of terminally aligned duplex states and internally aligned duplex states requiring the formation of such tails (or loops) will be governed by the probability of formation of each such configuration which thereby directly affects the assay signal. In order to provide methods of quantitative analysis of experimental data obtained, also disclosed are several models of assigning probabilities to configurations differing in the number of duplex repeats.

BRIEF DESCRIPTION OF THE FIGURES

FIG. 2 depicts a probe with three repeats (attached to an encoded microparticle) in all possible full-duplex configurations formed between the probe and a target with six repeats, and wherein the probe (following elongation) generates a different signal when bound in the terminal position of the target than in other positions.

FIG. 3A is a plot of intensities resulting from hybridization-mediated elongation using different length probes (each of which when bound in the terminal position on the target generates a different signal than when bound in other positions) and a number of different length targets.

FIG. 9 depicts that where the probe has more repeat units than the target, loops can form in the probe.

DETAILED DESCRIPTION

Disclosed is a method of "counting" tandem repeats in one or more designated target sequences using one or more oligonucleotide interrogation probes, each such probe preferably lacking an anchoring sequence but containing one or more tandem repeat sequences that are complementary to the target tandem repeat sequence(s) of interest. The (multiplexed) analysis of several targets in a single reaction is permitted, by providing, for each target, one or more interrogation probes.

Figure 1:
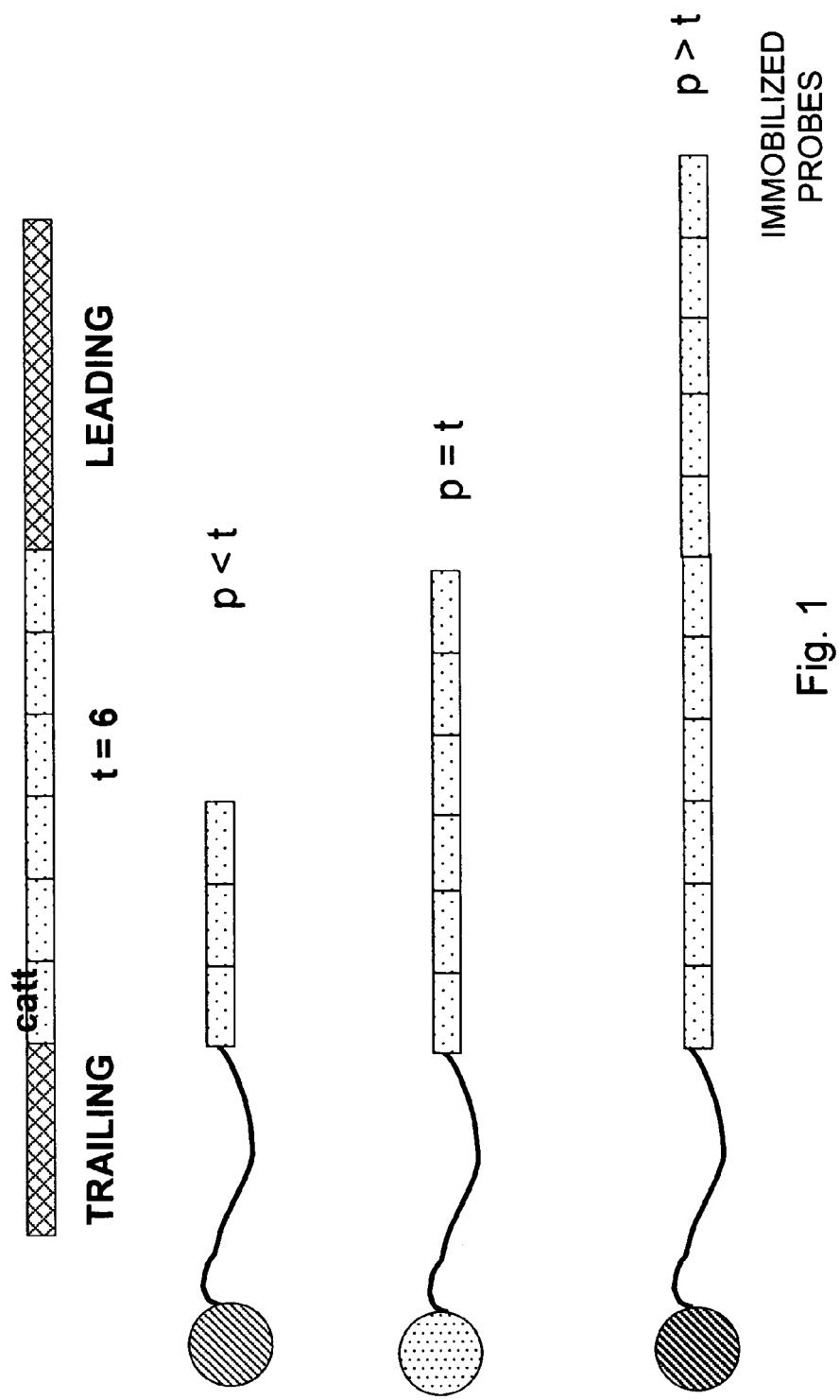
FIG. 1 depicts three different probes of different repeat lengths, encoded by attachment with different microparticles, and a target with six repeats.

Random Encoded Array Detection (READ)—Preferably, each of the one or more probes designed for the determination of the number of target repeats is attached, via its 5' end, to an encoded microparticle ("bead"), wherein the code—implemented by way of a color scheme, as shown in FIG. 1—identifies the sequence and length of the probe attached thereto.

I Low Temperature Regime

In general, in the low temperature regime, the operating temperature at which assay steps—including enzyme-mediated probe extension—are performed does not exceed the melting temperatures of the anticipated full duplex states. Conversely, it will be advantageous or necessary—for example in view of the requirement to perform the enzyme-mediated extension step at a certain temperature—to operate at a temperature which exceeds the melting temperatures of all anticipated partial and full duplex states. A high temperature regime is described herein in Section II.

I.1 Full Duplex Configurations: $p \leq t$

If the number of repeat sequences in the probe is p, and the number of repeat sequences in the target is t, then, provided that p is less than t (p<t), probe and target can hybridize—with equal likelihood—in any of $t-p+1$ possible "full duplex" configurations involving the entire length of the probe, said configurations differing only in the phase of alignment. For example, the possible duplex configurations formed between a probe with three repeats and a target with six repeats are shown in FIG. 2: one unique "terminal alignment" configuration, wherein the probe is aligned with the "5'-terminal" nucleotide in the target repeat, and three of "internal alignment" configurations wherein the probe is aligned with "repeat-internal" nucleotides in the target repeat.

This description applies when duplex configurations involve the full length of the probe ($p \leq t$) or the target (p>t) such that all full-length duplex repeat configurations, independent of the phase of the alignment, are realized with equal probability. Equal probabilities would be consistent with the evaluation of the free energy of duplex formation in terms of only the subsequences participating in the formation of the duplex. All full-length duplex configurations involving p repeats will then have the same free energy, that is, they will be "degenerate" configurations. More generally, however, also described is the more complex scenario involving partial duplex configurations as described in detail in Section II below.

Differential Labeling of Duplex Configurations in Terminal and Internal Alignment—

Differential labeling of the terminally aligned duplex states and the internally aligned duplex states, for example by way of single base extension using differentially labeled ddNTPs as disclosed herein, permits the "counting" of target repeats using one or more probes containing a known number of probe repeats.

Each probe is selected such that upon hybridizing with a target repeat in a "5'-terminal" alignment—that is, in a configuration placing the probe's 3' end in juxtaposition to the "5'-terminal" nucleotide in the cognate target's tandem repeat, the "5-terminal" nucleotide being that nucleotide in the target repeat located immediately adjacent to the 5' flanking sequence—the probe is labeled with a first color ("Orange" in FIG. 2), and upon hybridizing with a target repeat in a "repeat-internal" alignment—that is, in a configuration placing the probe's 3' end in juxtaposition to a nucleotide located in the "interior" of the cognate target's tandem repeat and hence not immediately adjacent to the 5' flanking sequence—the probe is labeled with a second color ("Green" in FIG. 2) differing from said first color. Preferably, labeling is accomplished by template-mediated single nucleotide extension of the probe's 3' end, for example by addition of a labeled dideoxynucleotide triphosphate (ddNTP) by methods well known in the art. Alternative methods, for example probe elongation by incorporation of individual labeled deoxynucleotide triphosphates (dNTPs), also can be used.

Repeat Counting by Concurrent Analysis of Multiple Probe-Target Configurations—

The analysis of the results of the hybridization and labeling reactions described above permits the determination of the number of target repeats as follows. Generally, out of $t-p+1$ possible configurations of the duplex, there will be one full-length "5'-terminal" ("external") alignment, labeled in the first color ("I-Orange"), and t–p full-length "internal" alignments, labeled in the second color ("I-Green"). Consequently, the intensities of green and orange signal recorded from the assay will be of the form $I_E = I\text{-Orange} \sim 1/(t-p+1)$ and $I_I = I\text{-Green} = (t-p)/(t-p+1)$ Accordingly, the proportion of I-Green to I-Orange recorded from the array of probes following extension is proportional to (t–p):

$I_I/I_E \sim t-p$

Examples of calculated profiles are shown in the Examples included herein.

Determination of Target Repeat Number, t:—Applying this information relating to intensity ratios permits the determination of an unknown number of repeats in a target, x, preferably in an assay configuration providing internal calibration of the recorded intensity ratios. For example, a single probe can be used in combination with a reference target containing a known number of repeats identical in composition to those in the target of interest by comparing said proportion of red and green labels obtained in separate interactions of the probe with the reference target and with the target of interest.

Figure 3B:
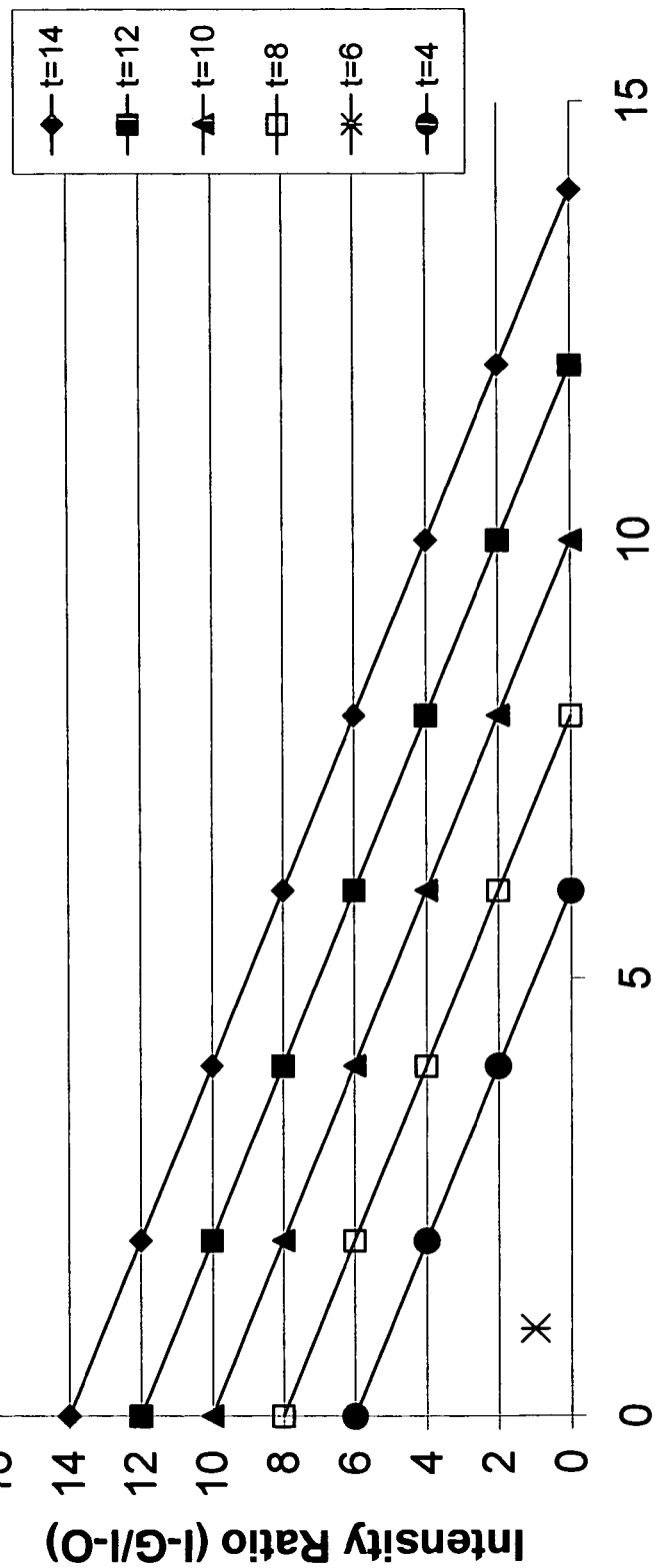
FIG. 3B is a plot of the intensity ratio resulting from hybridization-mediated elongation using different length probes (each of which when bound in the terminal position on the target generates a different signal than when bound in other positions, as in FIG. 3A) plotted against probe repeat number.

Multiple Probes—Successive determinations of target repeat numbers may be made by placing probes in solution so as to permit interaction with one target. Preferably, at least two probes—but no reference target—are used, each probe containing a known number of probe repeats, respectively $p_1 < t$ and $p_2 < t$, $p_1 \neq p_2$, to construct a standard plot: given that the ratio of intensities, I-Green/I-red, is proportional to t–p, the plot of I-Green/I-red vs p would appear as in right-hand panel of FIG. 3, permitting determination of the unknown number, x, of target repeats from the determination of the slope of the plot.

To simplify the analysis, partial duplex configurations, that is those containing alignments other than full-length alignments, may be destabilized by a suitable choice of temperature or experimental conditions. Preferably, the temperature of the assay may be adjusted so that, for each probe containing p probe repeats, only full-length duplexes, i.e., those containing p duplex repeats, are stable, but duplexes containing fewer than p duplex repeats are not. Alternatively, the assay temperature can be set to ensure stability of a duplex containing at least p–k, $1 \leq k < p$, duplex repeats; the operating temperature may be adjusted in the course of the assay to several values in accordance with a preset schedule to monitor the evolution of the multiple partial and full duplex configurations with temperature. Temperature scans will be particularly advantageous in order to identify the presence of multiple targets differing in the number of repeats, t.

"Offsets"—A modification in the design may be made to accommodate a configuration wherein the first nucleotide in the 5' ("downstream") flanking region of the target is the same as the nucleotide in the 3' ("upstream") terminal position of the target tandem repeat unit. Without modification in the assay design, probes hybridizing to the 5' terminal repeat section of the target will be extended by addition of the same nucleotide—and will thus carry the same label—as probes hybridizing to the target in "repeat-internal" alignments. A simple modification in probe design alleviates this ambiguity: two or more nucleotides are added to each probe, each of these nucleotides chosen to be complementary to a nucleotide in the target's 5' flanking region. This addition simply shifts each probe's 3' terminus to a position such that extension for "repeat-exterior" alignment produces the first color whereas extension of "repeat-internal" alignment produces the second color.

Figure 4:
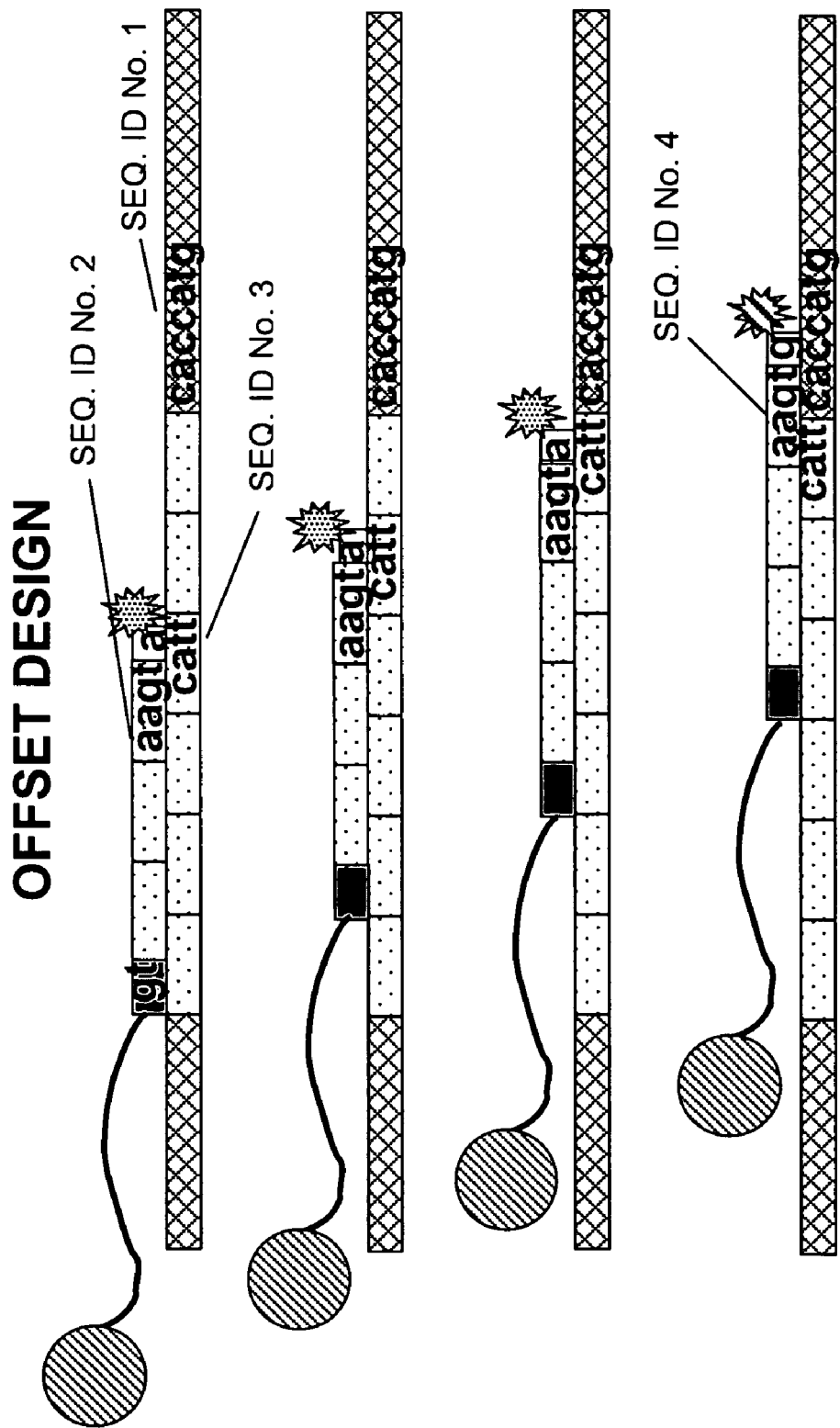
FIG. 4 depicts an "offset" encoded probe in all possible full-duplex configurations formed between the probe and a target with six repeats, and wherein the probe (following elongation) generates a different signal when bound in the terminal position of the target than in other positions.

In this same case, wherein the first nucleotide in the immediate 5' ("downstream") flanking region of the target is the same as the first nucleotide at the 3' ("upstream") end of the target tandem repeat unit, another design modification provides for the use of probes containing tandem repeats which are complementary to the nucleotides in the target repeat units, but are effectively offset, as illustrated in FIG. 4. That is, the probe repeat unit's first and last nucleotides are shifted with respect to the corresponding target repeat unit's first and last nucleotides. Appropriate selection of the first and last nucleotides in the probe ensures that the probe will be aligned such that its 3' terminal end is juxtaposed to a position other than the target repeat unit's 5' terminus. Upon probe extension, the nucleotide appended to the 3' end of the probe aligned near the target's 5' terminal flanking sequence is labeled differently from probes aligned in other positions.

I.2 Full Duplex States with Probe Overhangs (p>t)

Figure 5:
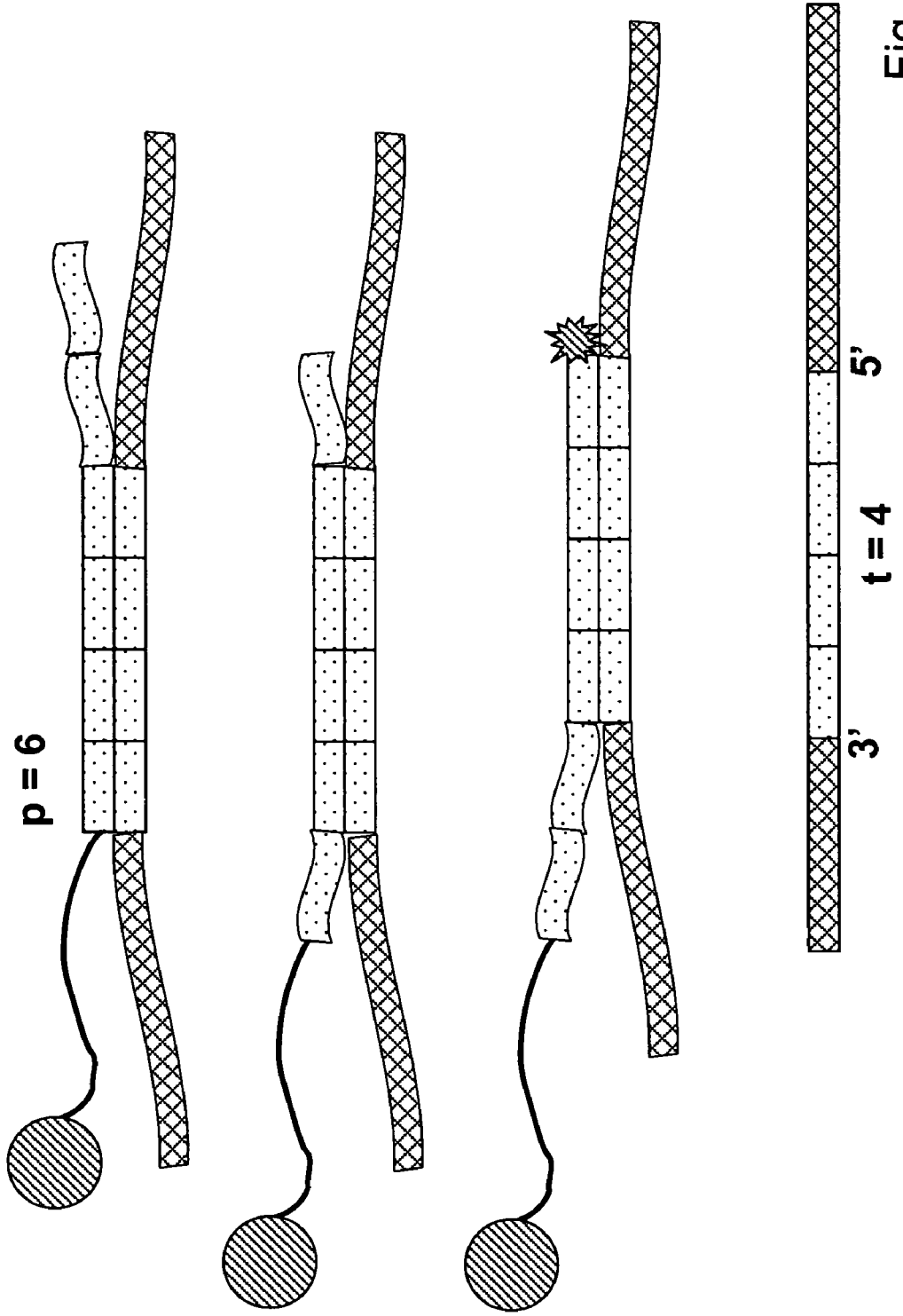
FIG. 5 depicts an encoded probe with six repeat units in all possible full-duplex configurations formed between the probe and a target with four repeats, and wherein the probe (following elongation) generates a signal only when it is bound such that its terminal position is aligned with the terminal position of the target.

Several extensions of this method of the present invention are also disclosed. One of these applies to the situation which arises when the number of probe repeats, p, exceeds the number of target repeats, t, as shown in FIG. 5. In such a case, full duplex configurations involve overlap of the t of the p probe repeats with the entire stretch of t target repeats, and only "5'-terminal" alignment will permit extension, given that all other configurations having t duplex repeats place the probe's 3' terminus in juxtaposition with a portion of the target's flanking sequence. That is, only the first color signal, but not the second color signal, will be produced (see FIG. 5). This observation thus serves as an indication that p is equal to, or exceeds t. Confirmation of this condition may be obtained by one of the following steps.

Reduction of Operating Temperature—First, the assay temperature may be lowered to a value permitting the formation of stable duplex with fewer than t duplex repeats. The evaluation of the free energy of duplex formation in terms of participating subsequences, in the manner universally applied in the field of molecular biology for purposes of calculating "melting temperatures," invokes a model of summing over free energy contributions associated with stacking interactions between nearest-neighbor base pairs in the duplex. Letting T denote temperature, and γ denote the average free energy per base pair, the "condensation" energy of a duplex of length N will be of the form $F_{Cond}/T \sim \gamma N$; that is, the stability of the duplex increases as a function of its length.

The elimination of each duplex repeat will lower the melting temperature, $T_M$, of the duplex by a constant decrement so that the temperature, T, can be adjusted to as to permit formation of duplexes having d=t–1 repeats, but not of duplexes having d=t–2 repeats: $T_M(d=t-2) \leq T < T_M(d=t-1)$. The appearance of the second color in response to the lowering of the temperature to the appropriate range therefore will confirm that $p \geq t$. Further lowering of the temperature, permitting formation of partial duplexes with even fewer repeats, will lead to a further increase in the strength of the second signal in a manner which reflects the increasing number of possible configurations permitting "repeat-internal" alignment.

Figure 6:
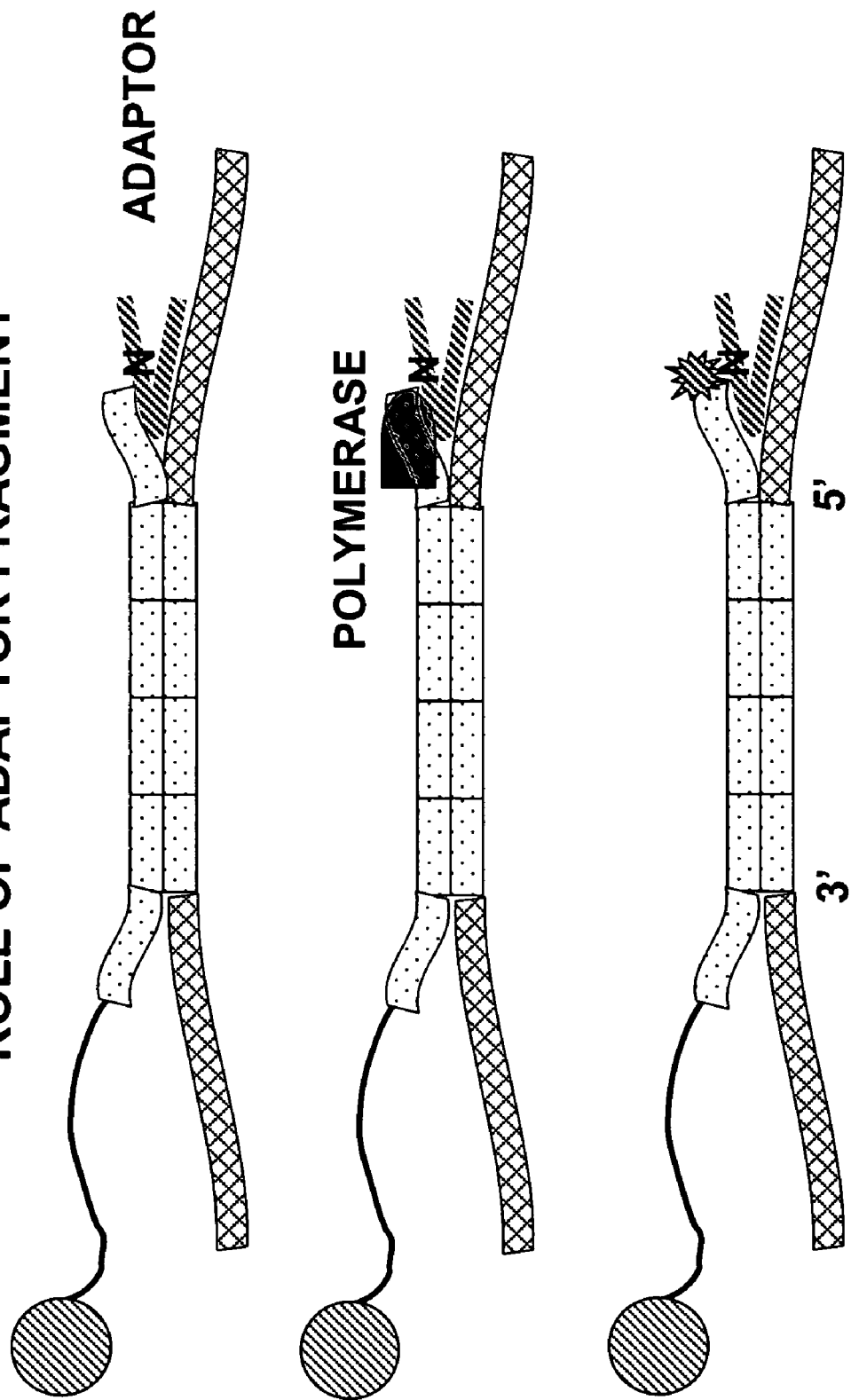
FIG. 6 depicts an adapter fragment has at least two portions, one of which is complementary to a flanking region adjacent to the 5' end of the target repeat and one of which is complementary to a probe repeat unit, and which generates a signal (following extension) when the probe is in the "one repeat overhang" position shown in the lower position in FIG. 6.

Labeling Configurations with 5' Overhangs: Adapter Sequences—Second, an oligonucleotide containing an adapter sequence ("adapter") may be included in the assay, as shown in the third and fourth schematics in FIG. 6. The adapter has at least two portions, one of which is complementary to a flanking region adjacent to the 5' end of the target repeat and one of which is complementary to a probe repeat unit. The hinge region of the adapter, serving only the function of holding the adapter in place once hybridization has taken place, may be composed of "neutral" nucleotides capable of forming a bond with any of the four specific nucleotides. The latter portion of the adapter includes at least one additional nucleotide, designated "N," that is juxtaposed to a nucleotide added to the 3' end of the probe. For example, when the probe is in the "one repeat overhang" position shown in FIG. 6, it can be extended at its 3' end with a unique ddNTP that is complementary to nucleotide N, and labeled with a unique third color ("red" in FIG. 6) which differs from the first and second colors, such as green and orange, used to identify probe extension in the situations described above. The appearance of the third color ("Red") in response to the addition of an adapter and an appropriately labeled nucleotide to the reaction mixture of interest, and the absence of signal indicating repeat-internal alignment, therefore confirms a probe to have a larger number of repeats than the target.

In one method of determining the number of target repeats, one can use a series of probes having increasing numbers of repeats in conjunction with an adapter, some of the probes having a number of repeats greater than, and others having a number smaller than the number of target repeats. In such case, to analyze one or more samples simultaneously, one would attach all the probes to encoded beads, the code identifying the length of the attached probe. The adapter and its labeling system will identify the presence of probes which have a greater number of repeats than does the cognate target in the sample.

Figure 7:
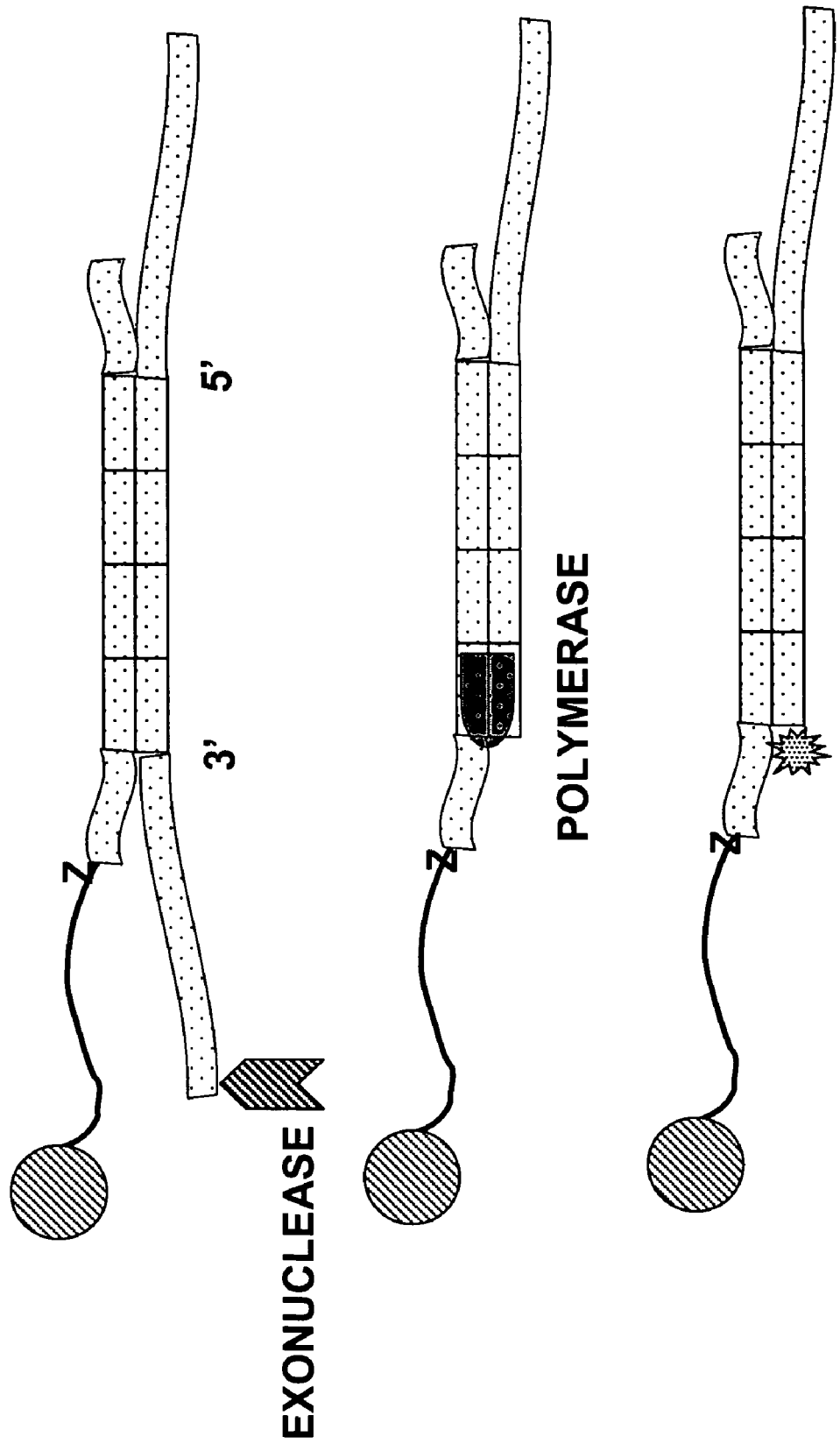
FIG. 7 depicts a target which may be enzymatically modified to permit target extension (and unique labeling) using the probe as a template.

Labeling Configurations with 5' Overhangs: Digestion of Tails—Third, the target may be enzymatically modified to permit target extension using the probe as a template. For example, a first nucleotide, designated "Z" in FIG. 7, may be inserted immediately adjacent to the 5' terminus of the first probe repeat unit, this first nucleotide being selected so as to differ from the nucleotide at the 3' end of the probe repeat unit. The strategy, as shown in FIG. 7, is to permit an exonuclease (e.g., exo 1) to digest accessible "overhanging" single-stranded portions of the target, progressing in the 3' to 5' direction and leaving the 3' end of the target's tandem repeat unit available for probe-mediated extension with labeled ddNTPs. Specifically, the target is extended in a second step with a nucleotide labeled with a first color ("green") when target and probe repeat units are aligned as shown in FIG. 7 or in equivalent configuration, and with a nucleotide matching the "Z" nucleotide in the probe sequence and labeled with a second different color ("Orange") otherwise. After determining the relative intensities of green to orange labels, using the plot shown in FIG. 3, one uses essentially the same method described in the associated text to determine the number of repeats in the unknown target—noting, however, that in this case I-Green/I-Orange is proportional to p–t.

II Partial Duplex Configurations

Figure 8:
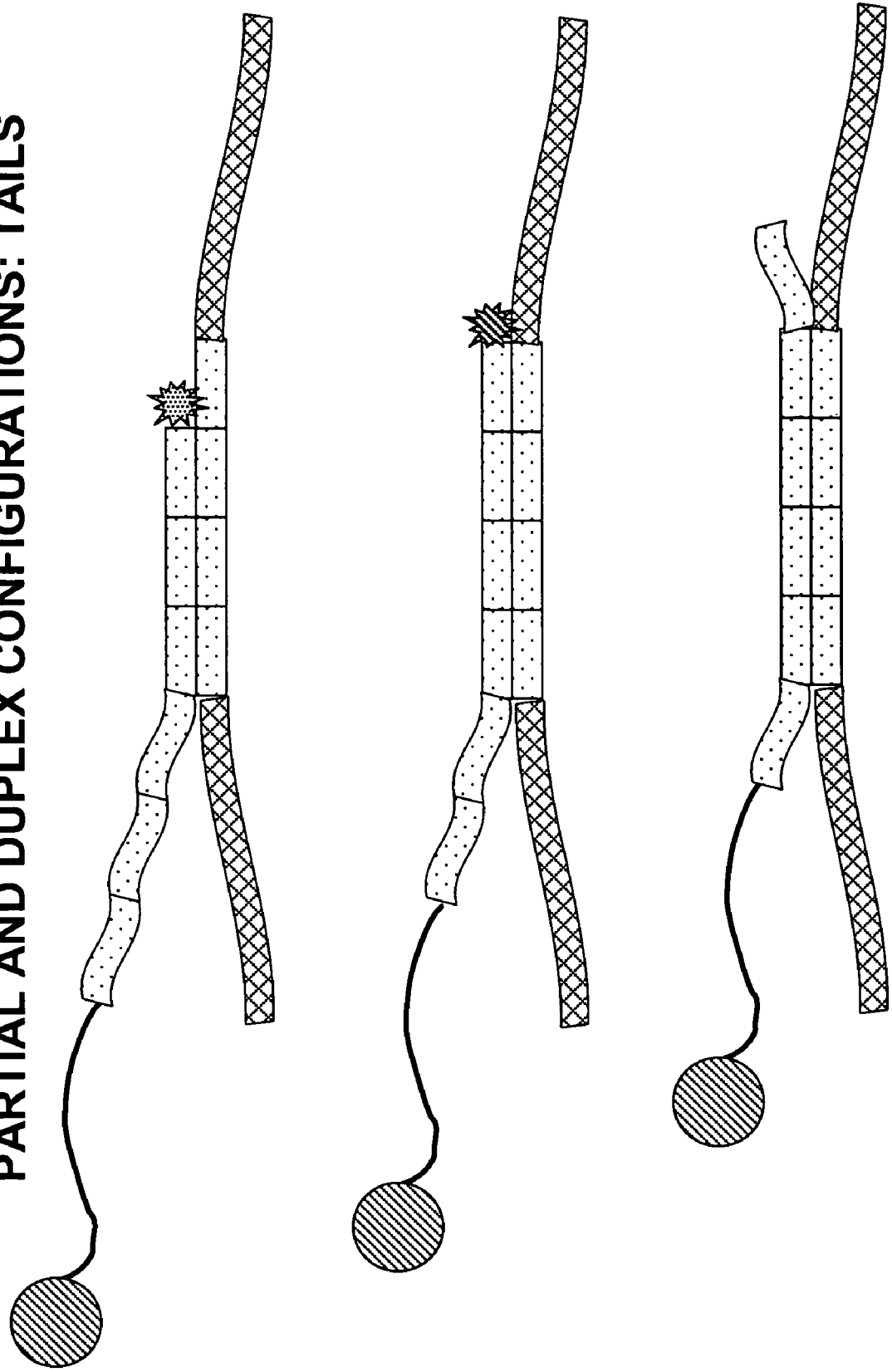
FIG. 8 depicts that one can have partial duplex configurations where the probe has more repeat units than the target (wherein the probe—following elongation—generates a different signal when bound in the terminal position of the target than in other positions).
Figure 10A:
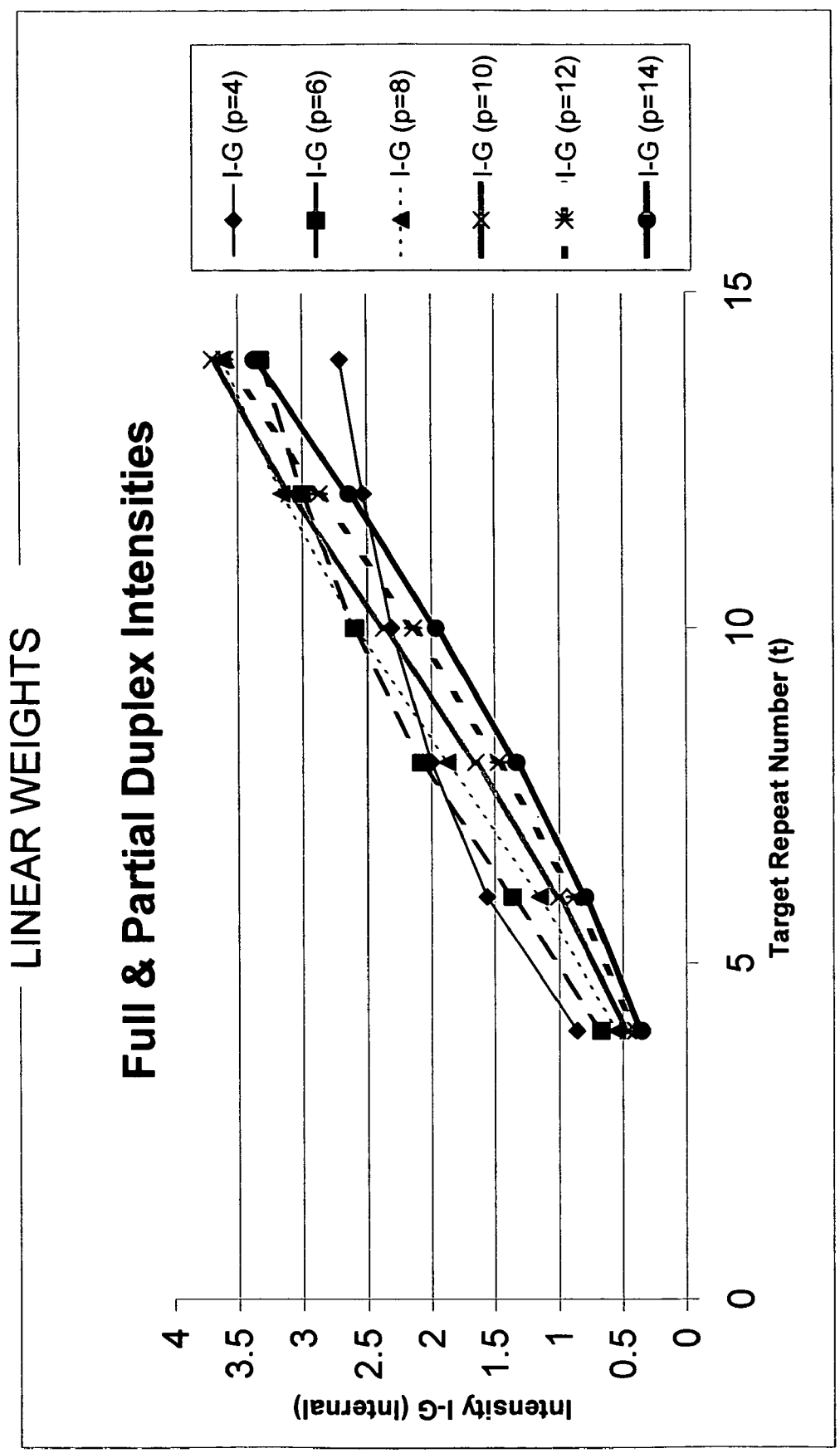
FIG. 10A is an intensity plot of probes bound in internal positions on the target against target length, of full and partial duplex intensities, with different length probes.
Figure 10B:
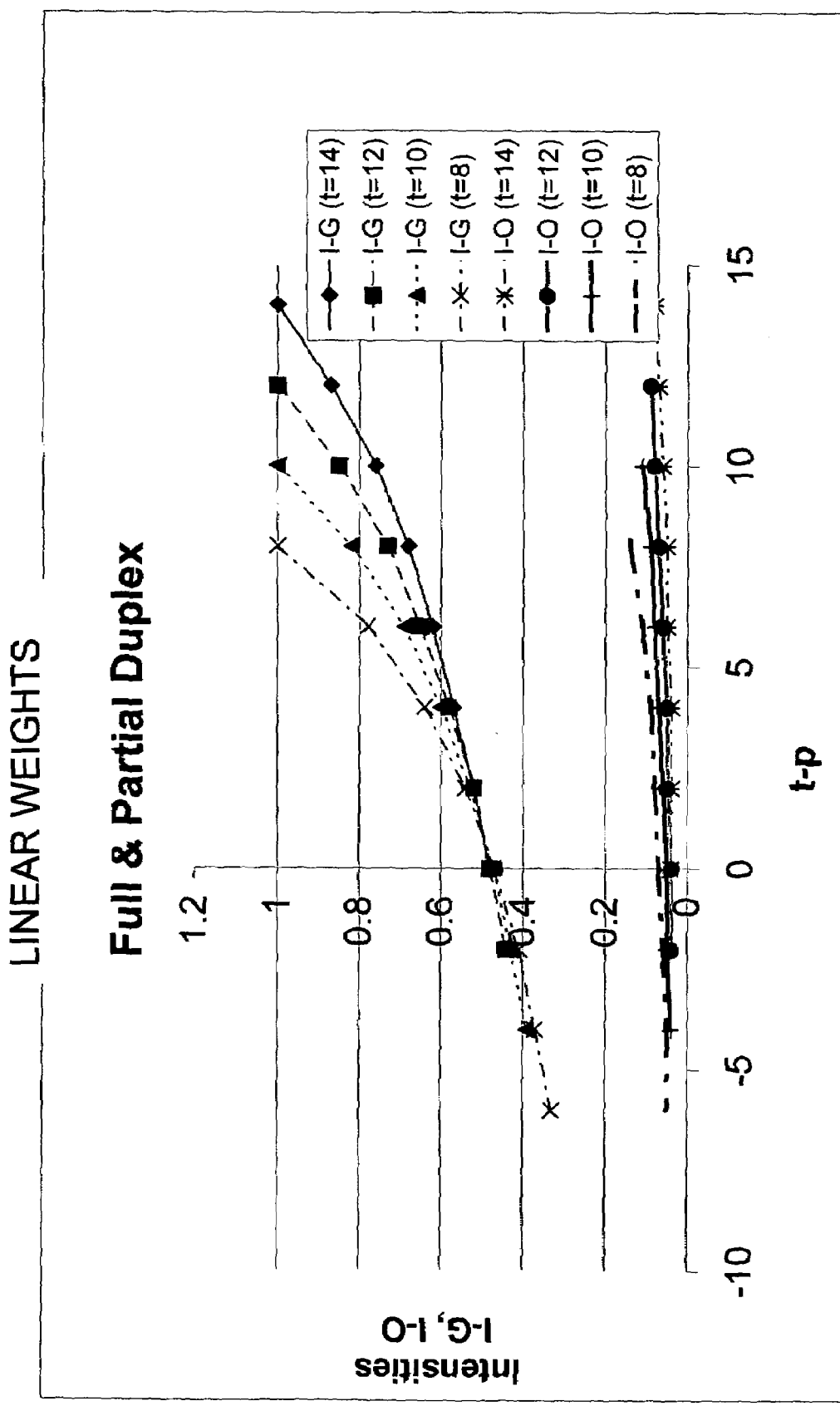
FIG. 10B is an intensity plot of probes bound in both internal and terminal positions on the target against target minus probe length, of full and partial duplex intensities.
Figure 10C:
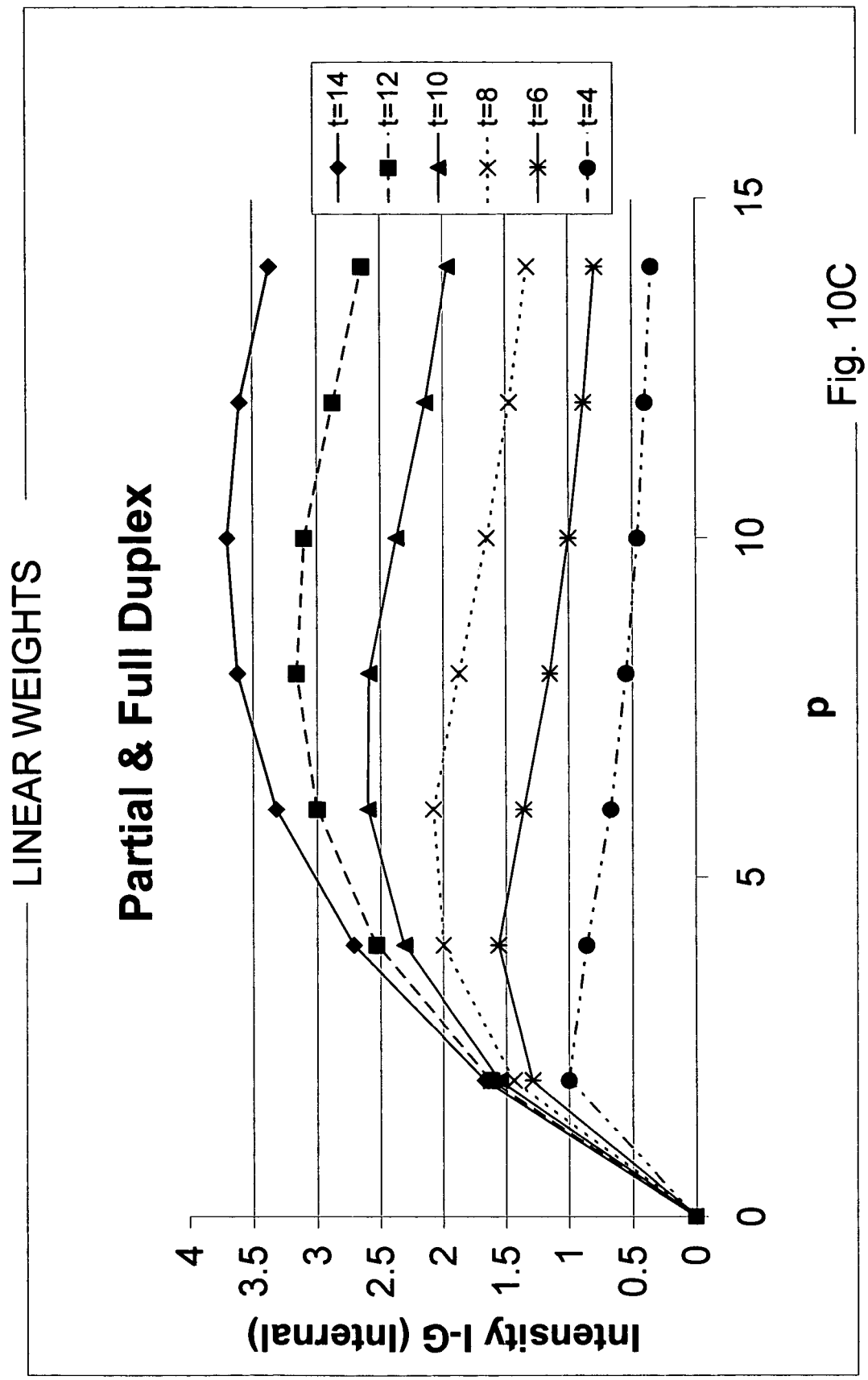
FIG. 10C is an intensity plot of probes bound in internal positions on the target against probe length, of full and partial duplex intensities, with different length targets.
Figure 10D:
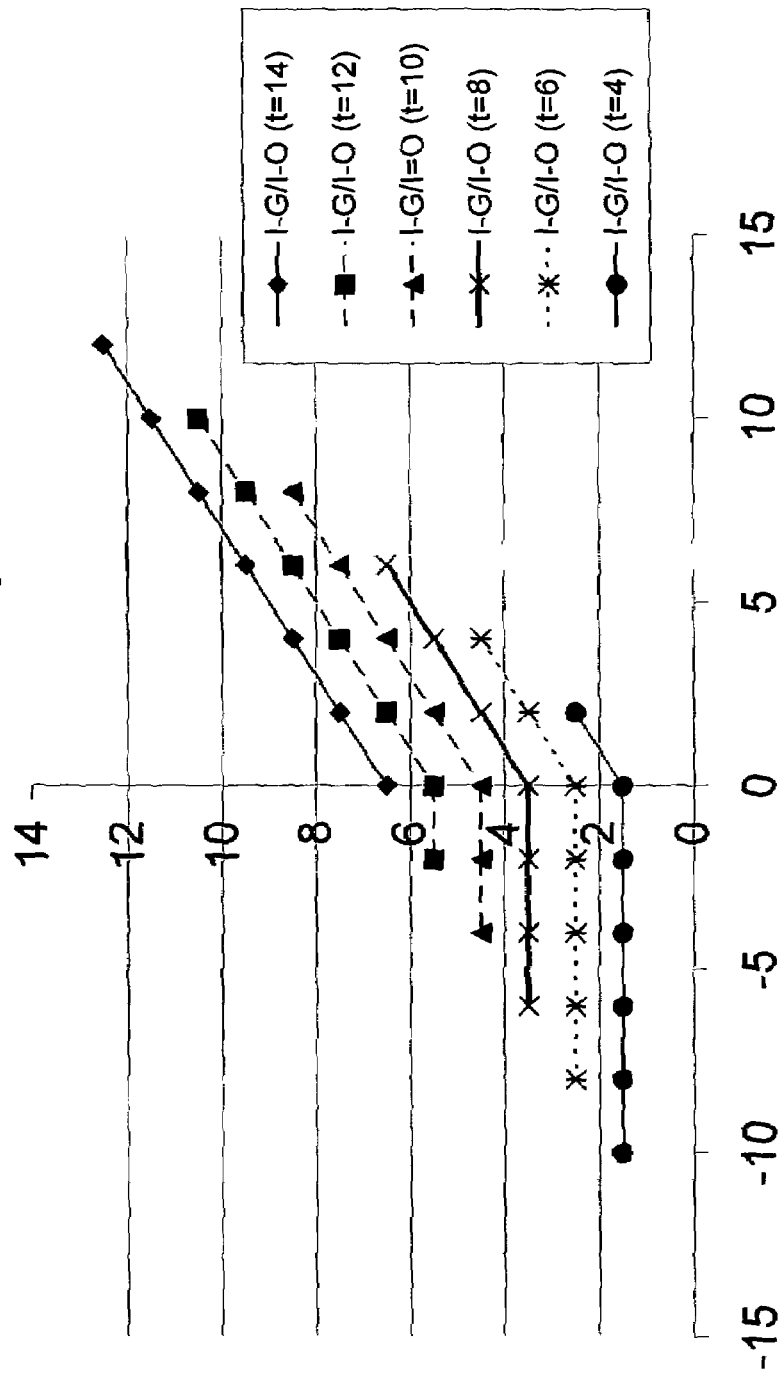
FIG. 10D is an intensity plot of the ratio of probes bound in internal positions on the target over probes bound in terminal positions on the target against probe length, of full and partial duplex intensities.
Figure 11A:
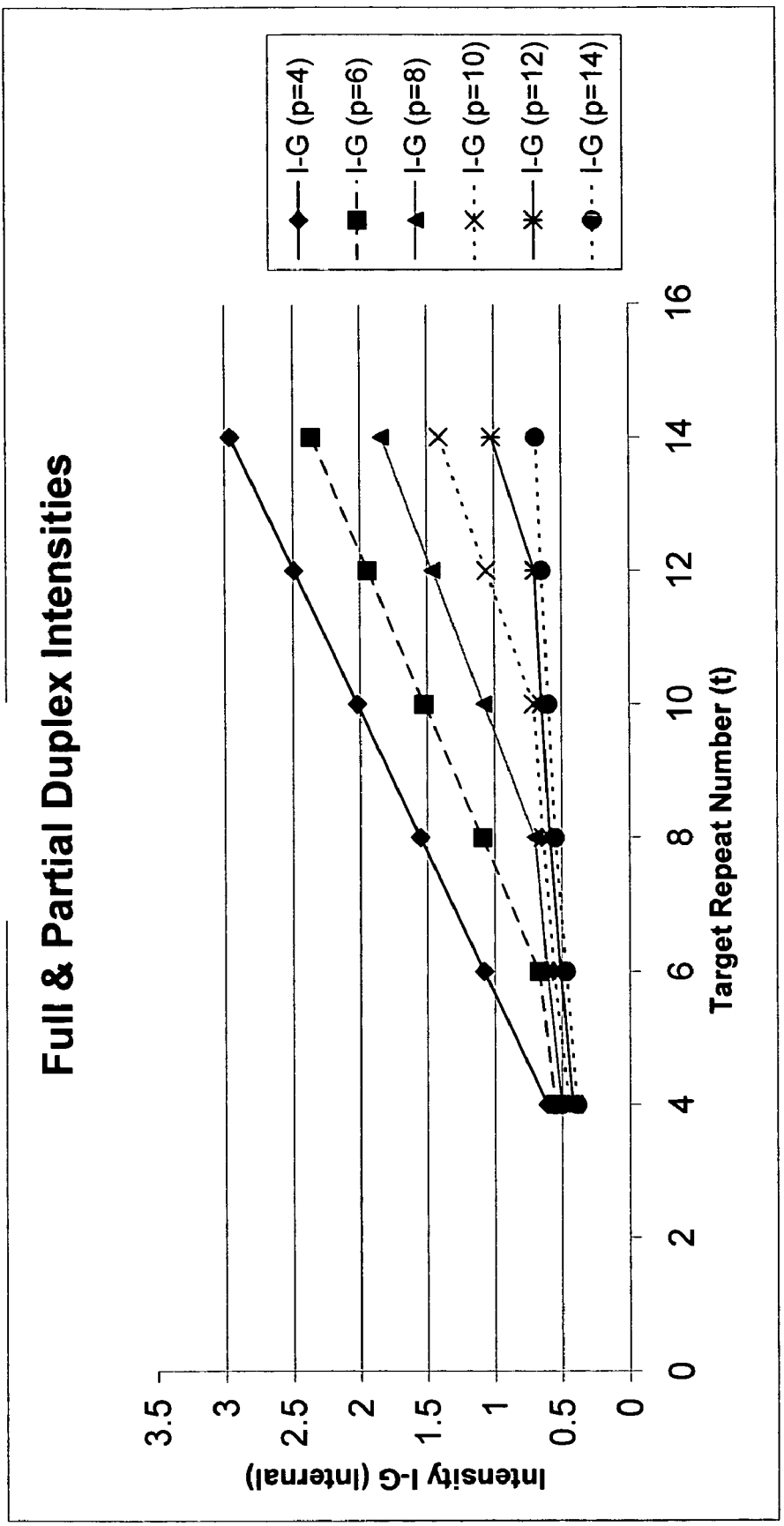
FIG. 11A is a model intensity plot of probes bound in internal positions on the target against target length, of full and partial duplex intensities, with different length probes, in a melting temperature model.
Figure 11B:
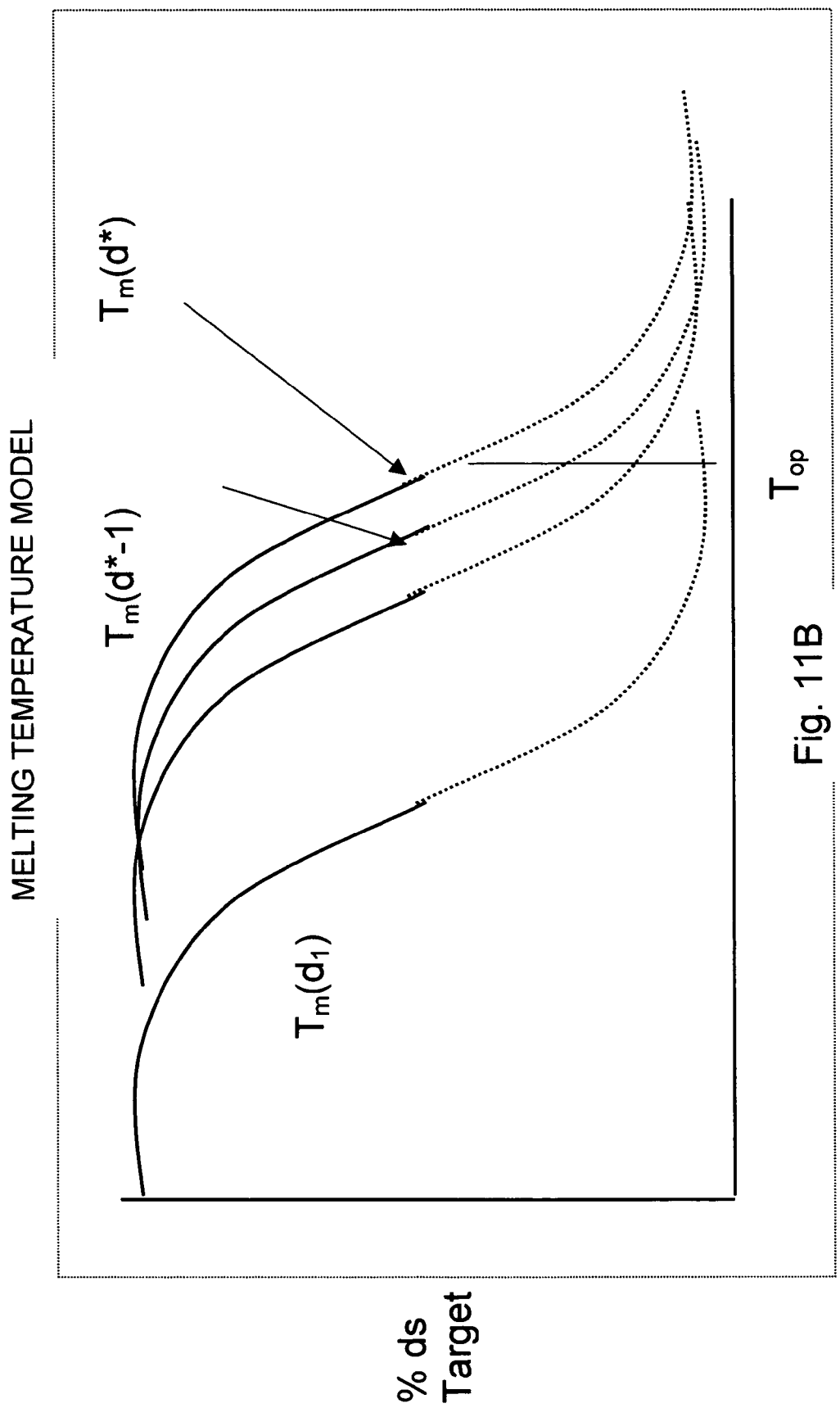
FIG. 11B is a model intensity plot of probes bound to target against temperature.
Figure 11C:
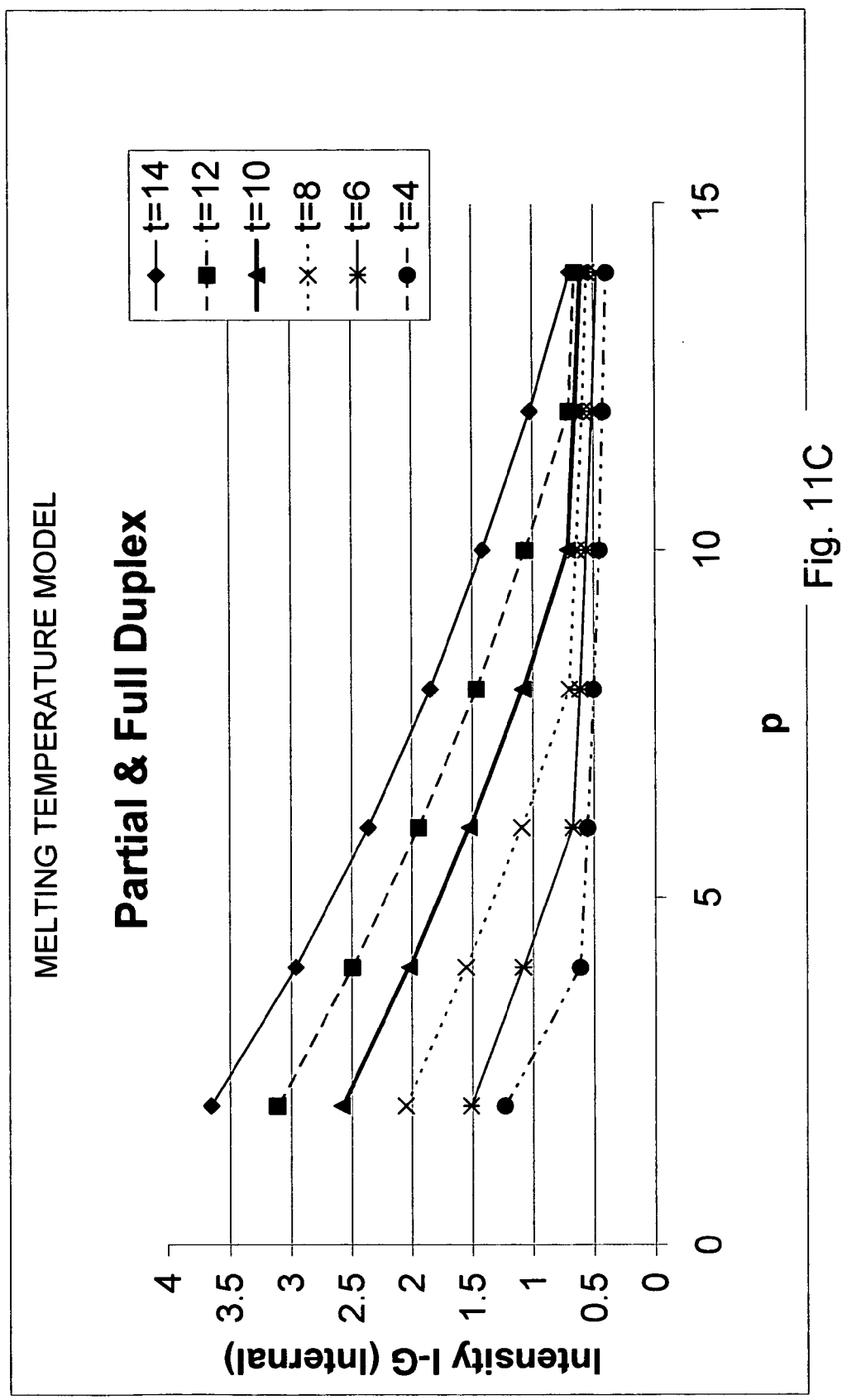
FIG. 11C is a model intensity plot of probes bound in internal positions on the target against probe length, of full and partial duplex intensities.
Figure 11D:
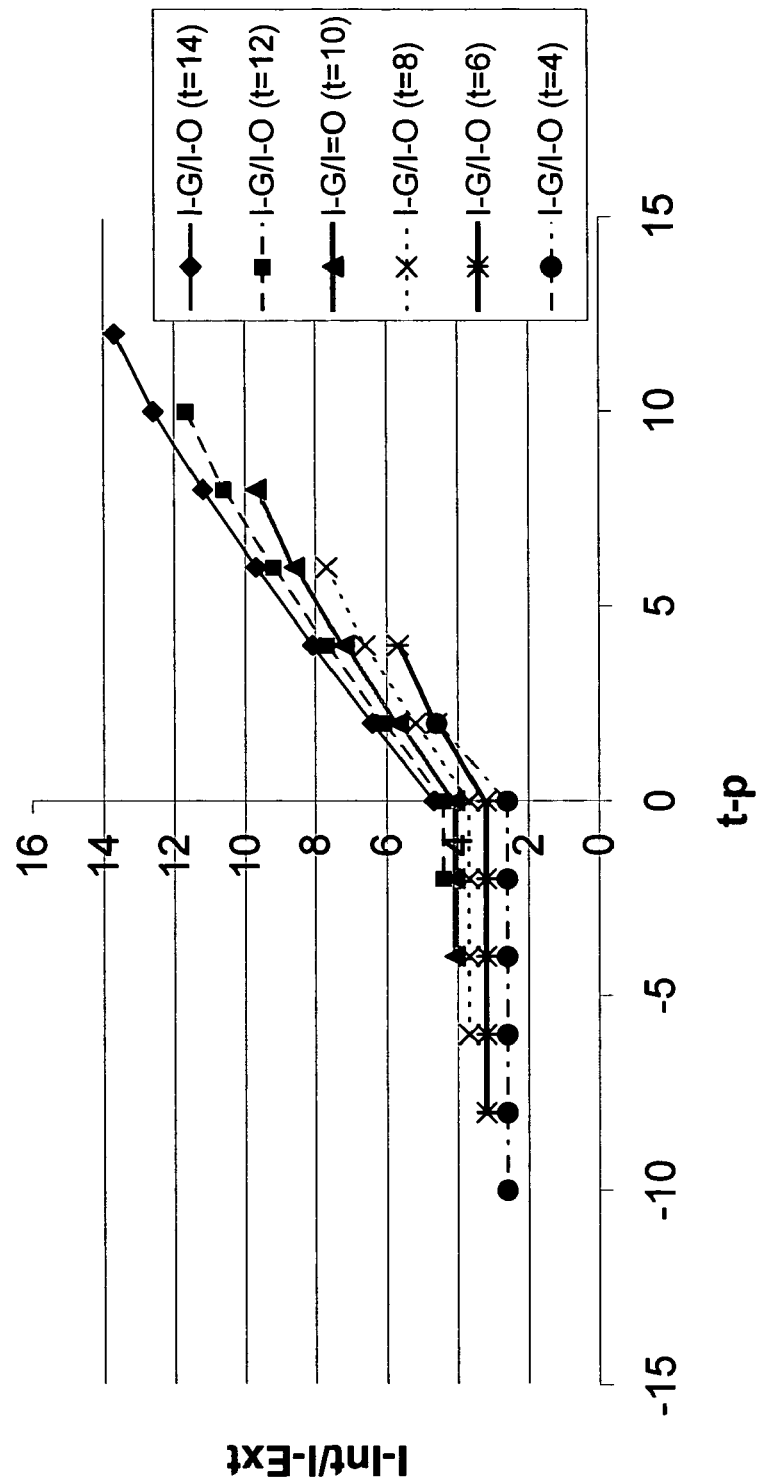
FIG. 11D is a model intensity plot of the ratio of probes bound in internal positions on the target over probes bound in terminal positions on the target against target minus probe length, of full and partial duplex intensities.
Figure 12A:
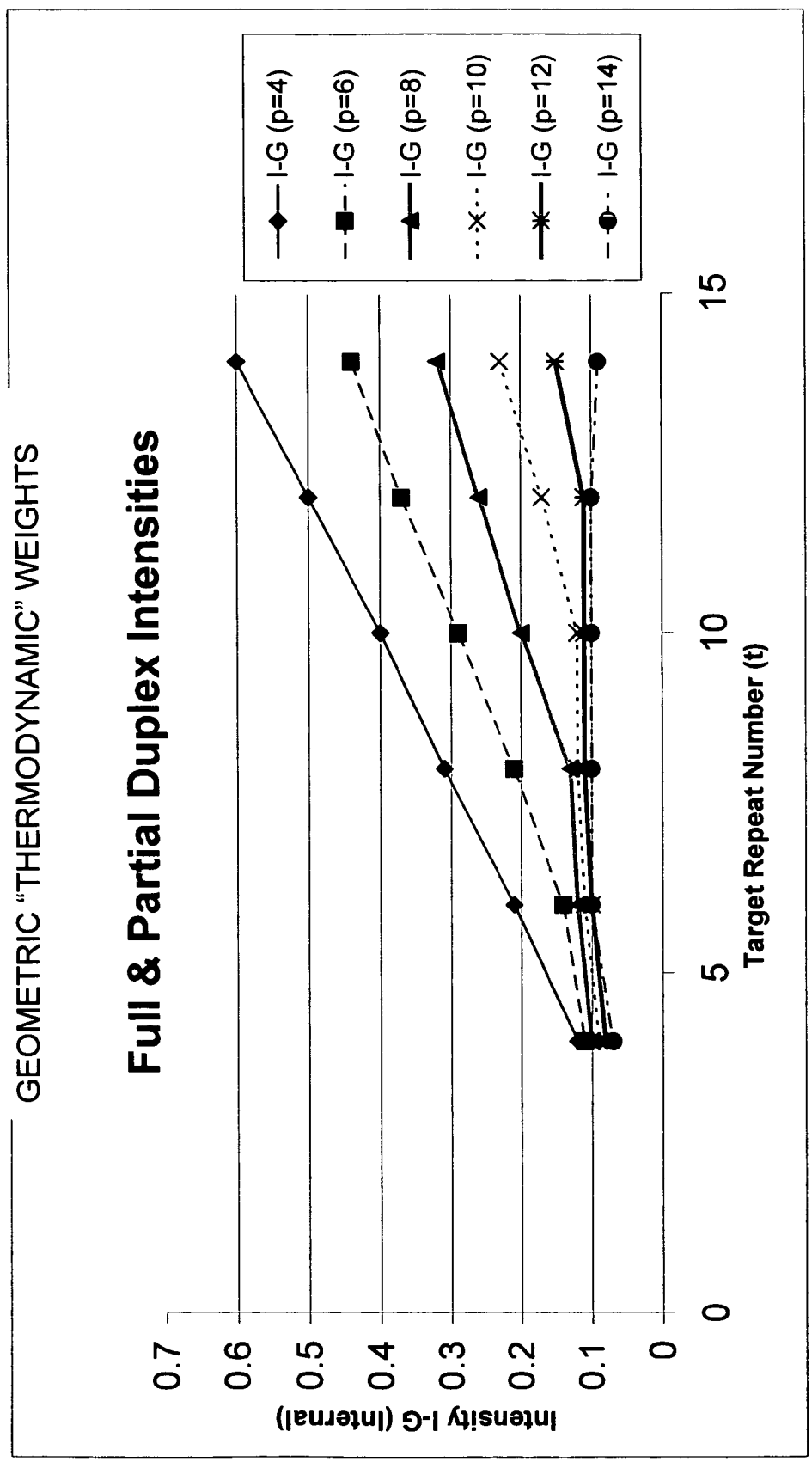
FIG. 12A is a model intensity plot of probes bound in internal positions on the target against target length, of full and partial duplex intensities, with different length probes, in a thermodynamic weight model.
Figure 12B:
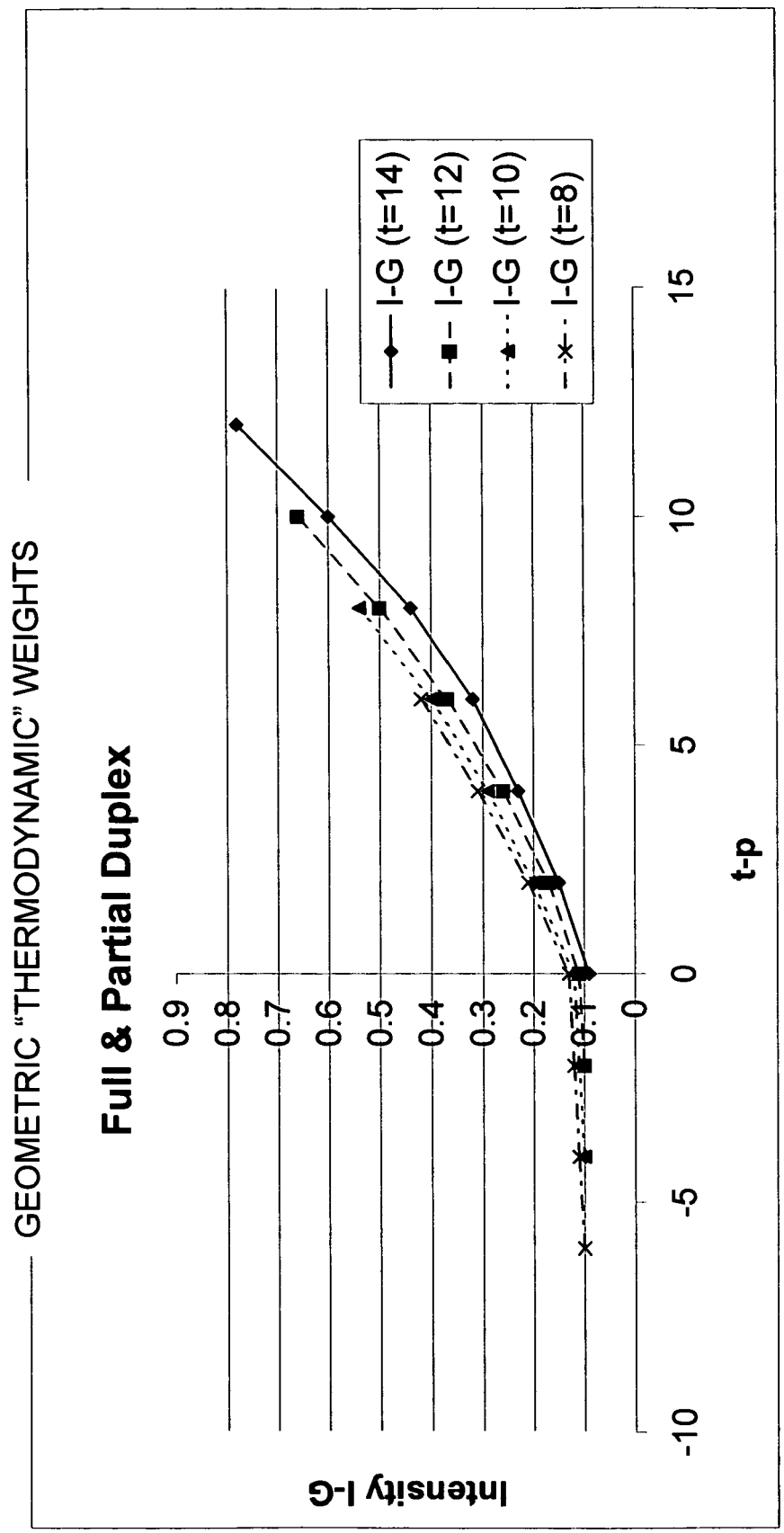
FIG. 12B is a model intensity plot of probes bound in internal positions on the target against target minus probe length, of full and partial duplex intensities, in a thermodynamic weight model.
Figure 12C:
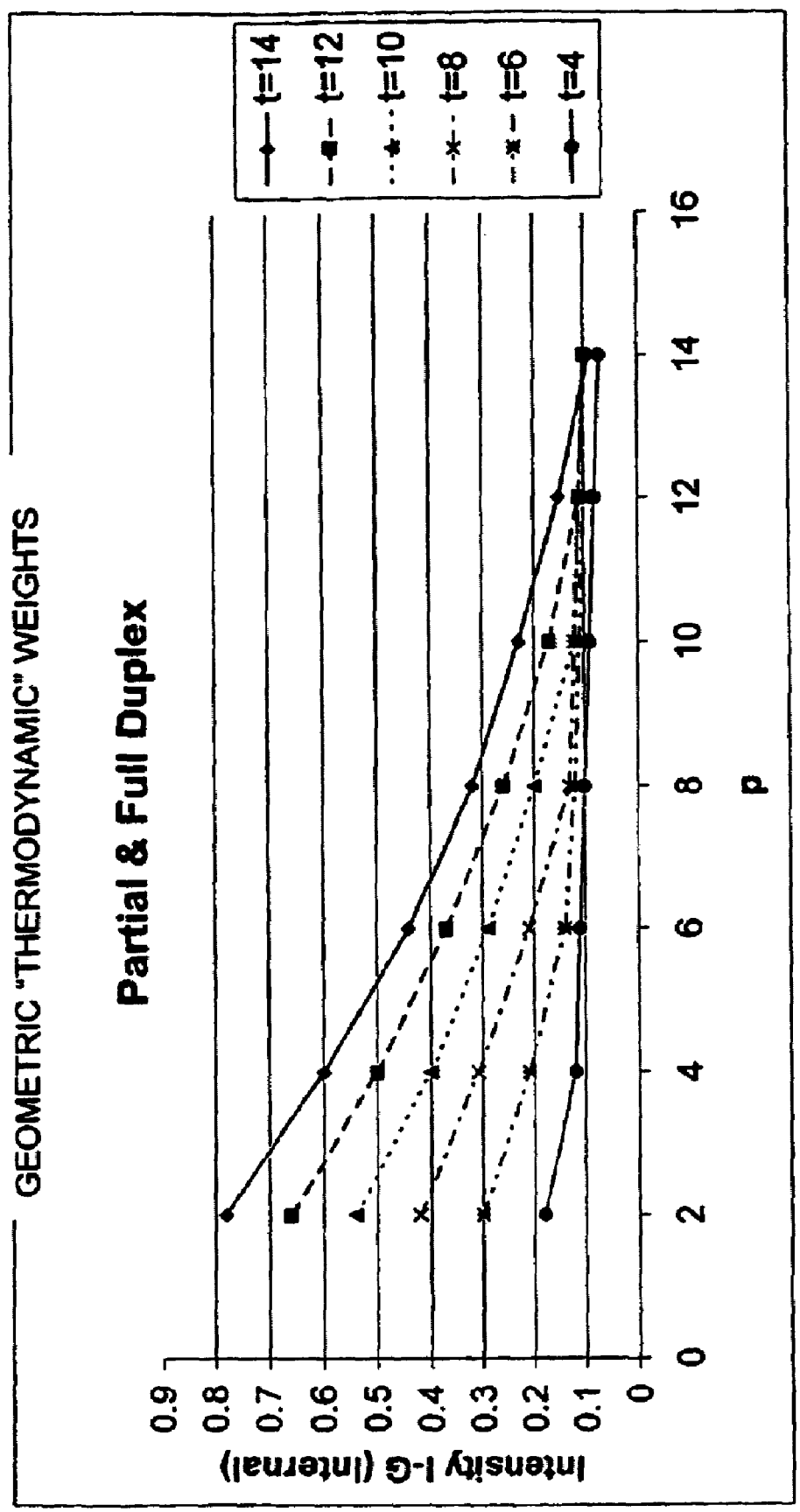
FIG. 12C is a model intensity plot of probes bound in internal positions on the target against probe length, of full and partial duplex intensities, with different targets, in a thermodynamic weight model.
Figure 12D:
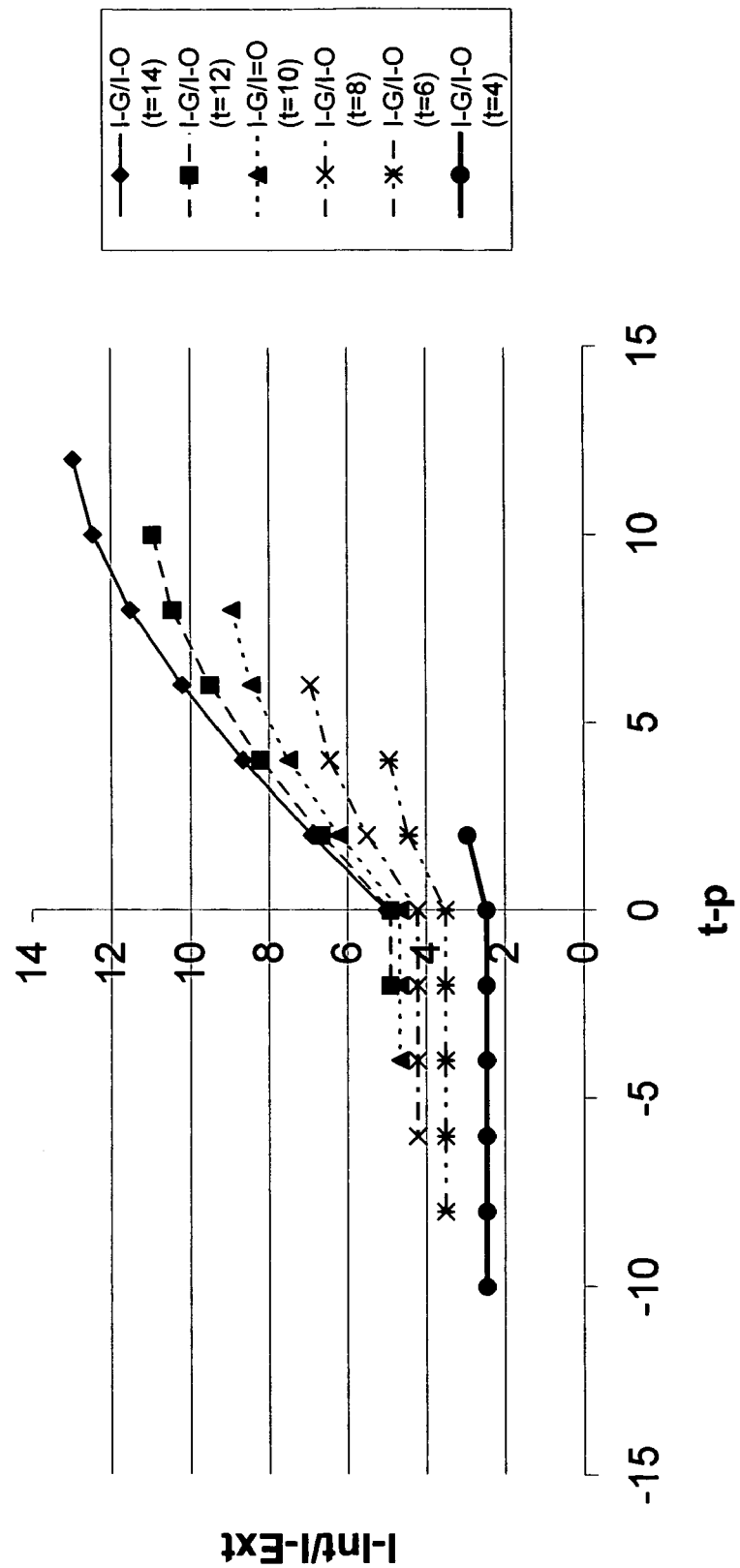
FIG. 12D is a model intensity plot of the ratio of probes bound in internal positions on the target over probes bound in terminal positions on the target against target minus probe length, of full and partial duplex intensities, in a thermodynamic weight model.

The aforementioned analysis of full duplex configurations to the analysis of the full set of configurations involving "tails" (FIG. 8) including partial duplex configurations in which the number of duplex repeats, d, is smaller than either the number of probe repeats, p, and the number of target repeats, t. Slippage, that is, shifts in the phase of the alignment of probe-target repeats, must be anticipated especially in the absence of chosen "anchor" sequences flanking the probe repeats on the 3' or 5' side. In addition to tails, "loops" also may form (FIG. 9).

The presence of partial duplex configurations manifests itself in experimental data, for example, in the form of finite green signal intensity recorded under the condition t–p=0. The presence of loops will manifest itself in the form of higher than expected green and orange signals recorded under the condition t<p.

Partial Duplex Configurations with Tails: Serial Product—Given a probe containing p repeats and a target containing t repeats, the set of all possible partial and full duplex configurations is readily enumerated by representing probe and target repeats by strings of 1's and computing the serial product of the two strings. For example, with p=3, t=5, the serial product of <1 1 1> and <1 1 1 1 1> produces the string <1 2 3 3 3 2 1> of length 3+5–1. Generally, the serial product of a string P of length p and a string T of length t will be a string, P*T, of length t+p–1, each field of the string giving the number of duplex repeats in the corresponding configuration and thus representing the density of states. The serial product is conveniently evaluated by resorting to matrix multiplication (Seul, O'Gorman and Sammon, "Practical Algorithms for Image Analysis", Cambridge University Press, 2000), as illustrated in Example III. Of the t+p–1= (t–p+1)+2(p–1) possible configurations, t–p+1 are degenerate full duplex configurations, 2(p–1) are partial duplex configurations.

Heterozygosity: Two Targets of differing Repeat Numbers—In the context of applying tandem repeat analysis to identity typing, samples typically will be heterozygous for repeat number polymorphism. That is, the analysis must reveal the presence of, and identify, two target strands, $T_1$ and $T_2$ of differing repeat numbers, $t_1=t(T_1) \neq t_2=t(T_2)$. The set of corresponding duplex configurations is readily evaluated using the distributive property of the serial product: $P*T_1 + P*T_2 = P*(T_1+T_2)$, yielding a string of length $\max(t_1, t_2)+p-1$. The resulting density of states will differ from that of either target alone, as illustrated in Example III.

III Non-degenerate Configurations: Weights

In certain instances, as in the case of a certain range of preferred extension temperatures, the assay may require an operating temperature that exceeds the nominal "melting" temperatures of some duplexes, $T_M(d=1)<T_M(d=2)$, . . . $<T< . . . <T_M(d=\min(p, t))$, or all duplexes, $T_{M(d=1)}<T_M(d=2), . . . <T_M(d=\min(p, t))<T$. This condition generally will favor the formation of partially or completely denatured probe-target duplex states in which all configurations displaying d duplex repeats will be formed with a certain probability, w(d).

Partially or completely denatured probe-target duplex states generally will not all form, or may not all be subject to labeling, with equal probability. Disclosed, therefore, is a method to introduce weight functions, w=w(d), reflecting the probability of formation of labeled duplex configurations.

The weight functions are used herein to model the probability of formation of an observable configuration which requires a first step of annealing of target (T) to a probe (P) and a second step of labeling of the probe-target complex (PT), for example by way of single-base extension, requiring the reaction of the complex with an enzyme (E) and the reaction of the resulting complex with labeled substrate (S*) to produce the labeled probe, (S*–P).

wherein each reaction equilibrium is governed by a pair of kinetic rate constants, $k_{ON}$ and $k_{OFF}$. The reaction involves the recycling of target ("template") as well as enzyme, permitting for isothermal "accumulation" of labeled product, S*–P. In this regard, the multiplexed analysis of duplex repeat configurations illustrates the more general case of elongation or extension-mediated multiplexed analysis of polymorphisms. Labeling with ddNTPs effectively removes one constituent ingredient, namely probe, from the reaction. In a preferred embodiment, labeled product is immobilized by attachment to a solid phase carrier such as an encoded microparticle.

Setting $d^*=d_{max}$, wherein $d_{max}=p$ for $t \geq p$ and $d_{max}=t$ for $t<p$, that is, $d^*=\min(p, t)$, expressions for the total intensity, $I_E$, of 5'-terminally aligned states, and the total intensity, $I_I$, of internally aligned states, are readily evaluated:

$$I_E = w(d^*)/t+p-1$$

and $$I_I = w(d^*)\{\Sigma_{(d=1) \text{ to } (d=d^*-1)}(w(d)/w(d^*))+(t-p)\}/(t+p-1) \quad p<t$$

or $$I_I = w(d^*)\{\Sigma_{(d=1) \text{ to } (d=d^*-1)}(w(d)/w(d^*))\}/(t+p-1) \quad p \geq t$$

Defining the function $H(x)$ to denote the step function $H=0$, $x \leq 0$, $H(x)=1$, $x>0$; permits the use of the compact notation $$I_I = w(d^*)\{\Sigma_{(d=1) \text{ to } (d=d^*-1)}(w(d)/w(d^*))+(t-p)H(t-p)\}/(t+p-1)$$

Defining the function
$g_d=2$; $d<d^*$
$g_d=t-p$; $d=d^*$ to denote the multiplicity of each duplex configuration, the expressions for $I_E$ and $I_I$ are seen to represent partial sums contributing to the partition function $$Z = 1/(t+p-1)\Sigma_{(All\ Duplex\ Configurations)}g_d w(d)$$

Also of interest is the ratio:

$$I_I/I_E = \{\Sigma_{(d=1) \text{ to } (d=d^*-1)}(w(d)/w(d^*))+(t-p)H(t-p)\}$$

Example IV illustrates the evaluation of these expression for specific weight functions, $w=w(d)$. The computed profiles will permit the analysis of experiments—for example, a set of "standard curves" may be computed to show the expected variation of intensities, $I_E$ and $I_I$, as a function of the number of target repeats, t, for partial duplex configurations formed between a target and two or more probes of $p_1, p_2, \ldots$, repeats, the $p_j$ preferably bracketing t. Alternatively, trial profiles may be employed in regression analysis of experimental data to determine t, the number of duplex repeats in the target.

III.1 The Role of Configurational Entropy in Duplex Formation

The "condensation" energy of a duplex of length N will be of the form $F_{Cond}/T \sim \gamma N$, T denoting temperature, and $\gamma$ denoting the average free energy per base pair. However, this contribution must be balanced against the loss in configurational entropy. The condensation of two flexible single nucleic acid strands into a "bound" state in the form of a "stiff" double-stranded (ds) duplex configuration containing d repeats reduces the number of configurations available to each strand in comparison to those available to each strand in its respective "free" state. For example, only a single state, namely the full duplex state, remains in the special case $d=p=t$, while for an unconstrained single chain of length $s \geq t$, the number of configurations, enumerated as the number of random walks on a lattice of coordination number z, varies as $\sim z^s$. Under this scenario, increasingly longer probe-target duplex configurations will be increasingly less likely, especially at high temperature.

Thus, duplex formation by way of the condensation of two single strands of length N from "random coil" configurations into a duplex of $d<<N$ repeats implies a loss of configurational entropy of the two original strands. As with the confinement of a polymer chain (deGennes, "Scaling Concepts in Polymer Physics", Cornell University Press, 1979), this condensation requires a deformation of the target strand so as to form the locally stiff duplex state with a probe strand which must undergo a similar deformation.

The free energy of deformation has the form $(F_{El}/T) \sim K(T)(L/L_0)^\delta$, where $L_0 \sim aN^\nu$, is the characteristic size of a free target strand containing N monomers of characteristic size a and L is the characteristic size of the target in the duplex state; $\nu(3d)=3/5$ and $\delta=1/(1-\nu)$ are exponents characterizing the statistical behavior of "real" polymer chains in good solvents. If that state contains $N_D$ monomers in d repeats (as does the probe), then $L_D = aN_D$ is the length of that "stiff" full duplex; the target "overhangs" thus contain a total of $N-N_D$ monomers and—assuming, for simplicity, an equal distribution of monomers between the two tails—have a characteristic size $L_T \sim a(\frac{1}{2}(N-N_D))^\nu$. Thus, $$F_{El}/T \sim (L/L_0)^\delta$$

$$\sim \left[2a\left(\frac{1}{2}(N-N_D)\right)^\nu + aN_D\right]^\delta / [aN^\nu]^\delta$$

$$\sim (2/2^\nu)[(1-N_D/N)^\nu + (N_D/N)N^{1-\nu}]^\delta$$

In the limit $N_D/N \sim 1$:

$$F_{El}/T \sim (2/2^\nu)[(N_D/N)N^{1-\nu}]^\delta \sim N_D$$

In the limit $N_D/N<<1$:

$$F_{El}/T \sim (2/2^\nu)[1+(N_D/N)(N^{1-\nu}-\nu)]^\delta$$

In the limit, $N_D/N \sim 1$, with $d \sim N_D$, the total free energy of duplex formation has the form $F/T \sim (K-\gamma)N_D$, wherein both the elastic constant, K, and the condensation energy per pair, $\gamma$, will depend (in generally differing form) on temperature, and $w(d) \sim \exp(-(K-\gamma)d/\Delta T)$, suggesting a model of geometric weights such as that discussed in Example IV. The constant $c=c(T)=\exp(-(K-\gamma)/\Delta T)$ changes sign at a specific transition temperature; when the entropic term dominates, formation of a duplex of increasing d will become increasingly less likely.

EXAMPLES

Example I

Calculated melting temperatures of duplex repeats in FES, a marker commonly used for parentage analysis, display a characteristic increment with the number of duplex repeats, permitting the choice of assay temperature so as to select a minimal number of repeats in thermodynamically stable duplex repeats:

|  | Duplex Repeats | | | | | | | |
|---|---|---|---|---|---|---|---|---|
|  | 4 | 6 | 8 | 9 | 10 | 11 | 12 | 13 |
| Calculated Melting Temperature (° C.) | 27.1 | 39.1 | 44.7 | 46.5 | 48.0 | 49.3 | 50.3 | 51.3 |

At $T=T_m$, a fraction of one half of the corresponding probe-target duplex configurations is "unbound", and this fraction increases as a function of increasing $\Delta T = T - T_m$. At a typical operating temperature of 60° C. for polymerase-mediated extension, all FES markers shown in the table will thus be predominantly in their unbound configuration.

Example II

Evaluation of the serial product of two strings yields a string containing the number of duplex repeats in each possible configuration; it is conveniently evaluated by matrix multiplication.

II.1 Serial Product of p=<1 1 1 1> and t=<1 1 1>:

```
1000000  1    1
1100000  1    2
1110000  1    3
1111000  0  = 3
1111100  0    3
0111110  0    2
0011111  0    1
```

II.2 Serial Product of p=<1 1 1> and t=<1 1 1 1 1>:

```
1000000  1    1
1100000  1    2
1110000  1    3
0111000  1  = 3
0011100  1    3
0001110  0    2
0000111  0    1
```

Target and matching probe sequences are mutually reverse complementary. The formation of duplex repeats thus corresponds to the parallel evaluation of the convolution of probe and target repeat sequences and represents an instance of parallel computation ("DNA computing").

Example III

In the tables below, full length duplex and partial duplex configurations with internal alignment are indicated in enlarged type, full length and partial duplex configurations with terminal alignment are indicated in the column with enlarged type, bolded, italicized type; the partial duplex configurations to the right of the column with enlarged type, bolded, italicized type will remain unlabeled (unless special steps are taken as described herein).

Duplex configurations formed by probes containing p=4, 6, 8, 10, 12 repeats with target containing t=8 repeats, obtained by evaluation of serial products of unit strings P, T.

| p | t + p − 1 | Duplex Repeats | | | | | | | | | | | | | | | | | |
|---|---|---|---|---|---|---|---|---|---|---|---|---|---|---|---|---|---|---|---|
| 4 | 11 | 1 | 2 | 3 | 4 | 4 | 4 | 4 | *4* | 3 | 2 | 1 | | | | | | | |
| 6 | 13 | 1 | 2 | 3 | 4 | 5 | 6 | 6 | *6* | 5 | 4 | 3 | 2 | 1 | | | | | |
| 8 | 15 | 1 | 2 | 3 | 4 | 5 | 6 | 7 | *8* | 7 | 6 | 5 | 4 | 3 | 2 | 1 | | | |
| 10 | 17 | 1 | 2 | 3 | 4 | 5 | 6 | 7 | *8* | 8 | 8 | 7 | 6 | 5 | 4 | 3 | 2 | 1 | |
| 12 | 19 | 1 | 2 | 3 | 4 | 5 | 6 | 7 | *8* | 8 | 8 | 8 | 8 | 7 | 6 | 5 | 4 | 3 | 2 | 1 |

Duplex configurations formed by probes containing p=4, 6, 8, 10, 12 repeats with target containing t=10 repeats, obtained by evaluation of serial products of unit strings P, T.

| p | t + p − 1 | Duplex Repeats | | | | | | | | | | | | | | | | | | |
|---|---|---|---|---|---|---|---|---|---|---|---|---|---|---|---|---|---|---|---|---|
| 4 | 11 | 1 | 2 | 3 | 4 | 4 | 4 | 4 | 4 | *4* | 3 | 2 | 1 | | | | | | | |
| 6 | 13 | 1 | 2 | 3 | 4 | 5 | 6 | 6 | 6 | 6 | *6* | 5 | 4 | 3 | 2 | 1 | | | | |
| 8 | 15 | 1 | 2 | 3 | 4 | 5 | 6 | 7 | 8 | 8 | *8* | 7 | 6 | 5 | 4 | 3 | 2 | 1 | | |
| 10 | 17 | 1 | 2 | 3 | 4 | 5 | 6 | 7 | 8 | 9 | *10* | 9 | 8 | 7 | 6 | 5 | 4 | 3 | 2 | 1 |
| 12 | 19 | 1 | 2 | 3 | 4 | 5 | 6 | 7 | 8 | 9 | *10* | 10 | 10 | 9 | 8 | 7 | 6 | 5 | 4 | 3 | 2 | 1 |

Duplex configurations formed by probes containing p=4, 6, 8, 10, 12 repeats with a mixture of two targets, one containing t=8 repeats, the other 10 repeats, obtained by evaluation of serial products of unit strings P and a string representing the sum of unit strings T(t=8) and T(t=10).

| p | t + p − 1 | Duplex Repeats |   |   |   |   |   |   |   |   |   |   |   |   |   |   |   |   |   |
|---|-----------|---|---|---|---|---|---|---|---|---|---|---|---|---|---|---|---|---|---|---|
| 4 | 11 | 1 | 2 | 4 | 6 | 7 | 8 | 8 | 8 | 8 | *8* | 6 | 4 | 2 |   |   |   |   |   |   |
| 6 | 13 | 1 | 2 | 4 | 6 | 8 | 10 | 11 | 12 | 12 | *12* | 10 | 8 | 6 | 4 | 2 |   |   |   |   |
| 8 | 15 | 1 | 2 | 4 | 6 | 8 | 10 | 12 | 14 | 15 | *16* | 14 | 12 | 10 | 8 | 6 | 4 | 2 |   |   |
| 10 | 17 | 1 | 2 | 4 | 6 | 8 | 10 | 12 | 14 | 16 | *18* | 17 | 16 | 14 | 12 | 10 | 8 | 6 | 4 | 2 |
|   |   | 1 | 2 | 4 | 6 | 8 | 10 | 12 | 14 | 16 | *18* | 18 | 18 | 17 | 16 | 14 | 12 | 10 | 8 | 6 | 4 | 2 |

Example IV

Weight Functions

In the cases considered below, c denotes a constant which generally will depend on experimental parameters such as temperature, ionic strength, pH as well as properties of fluorescent dyes or other labels used in creating the assay signal. More generally, to reflect differences in the chemical properties of dye labels or spectral variations in the optical response of the experimental apparatus employed to read intensities in the two color channels, it will be desirable to allow for the possibility of using two constants, $c_E \neq c_I$.

IV.1 Simple Trial Functions

IV.1.1 w(d)=c

In the presence of enzyme in large excess over target, any probe-target complex with matching configuration has an essentially equal chance of being recognized by enzyme, and—in the presence of labeled dNTP or ddNTP—extension will produce labeled probe regardless of the number of duplex repeats in the probe-target complex.

The expressions take the form:

$$I_E = c/t+p-1$$

and $$I_I = (c/t+p-1)\{(d^*-1)+(t-p)H(t-p)\}$$

Also of interest is the ratio:

$$I_I/I_E = (d^*-1)+(t-p)H(t-p);$$

IV.1.2 Linear Weights: w(d)=cd

If the formation of extended probe is governed by the formation of a duplex between probe and target, thermodynamic stability of the complex will increase with increasing d: the larger the number of duplex repeats of a given configuration, the more likely the probability, w(d) of formation of that configuration, and the more likely its being labeled by an enzyme-mediated extension reaction.

Using a simple trial function to represent the proportionality of w(d) to d, the expressions take the form:

$$I_E = cd^*/t+p-1$$

and $$I_I = (cd^*/t+p-1)\{½(d^*-1)+(t-p)H(t-p)$$

and, for the ratio:

$$I_I/I_E = \{½(d^*-1)+(t-p)\} = ½(p-1)+(t-p)H(t-p)$$

For the special case t=p=d*, these expressions simplify to:

$$I_E = \{ct/(2t-1)\}$$

and $$I_I = \{ct/(2t-1)\}½(t-1),$$

and, for the ratio:

$$I_I/I_E = ½(t-1)$$

The ratio profile permits the determination of t by determination of the intercept.

For the case $c_E = c_I = c$, intensity profiles, $I_E$, $I_I$ and $I_I/I_E$, as a function of t, p and t−p are shown in FIGS. 10A to 10D. In order to determine the number of repeats in a target sequence of interest, the target is permitted to form a duplex with two or more probes—preferably displayed on encoded beads—and the pattern of intensities for external and for internal termination is analyzed. For example, the intercept of the ratio $I_I/I_E = ½(t-1)$ FIG. 10D) permits the direct determination of t.

The profile for external termination displays a small decrease with t (FIG. 10B), reflecting the increase in the total number, t+p−1, of possible configurations, while the profile for internal termination displays an increase even for t−p=0, reflecting the formation of partial duplex configurations.

IV.1.3 High Temperature Regime: $w(d)=1/(T-T_m(d))$

In the high temperature regime, $T > T_m(d^*)$, under appropriate reaction conditions, the formation of labeled product by enzyme-catalyzed probe extension may be governed by the probability of forming a probe-target duplex containing d duplex repeats. This probability will decrease with $\Delta T(d) = T - T_m(d)$: the shorter d, the less likely the formation of the corresponding probe-target complex wherein $T_m(d)$ denotes the "melting" temperature, $T_m(d)$, of a complex containing d duplex repeats.

A simple trial function representing the high temperature portion ($T \geq T_m$) of a "melting curve" is obtained by assuming a constant increment $\delta T$ in melting temperature per addition of a single repeat and setting $$T_m(d) = T_m(d^*) - (d^*-d)\delta T$$

so that $$w(d) = 1/(T-T_m(d^*)+(d^*-d)\delta T)$$

or, with $C(d^*) = T - T_m(d^*)$:

$$w(d) = 1/(C+(d^*-d)\delta T)$$

Note that, since $d^* = \min(p, t)$, each probe-target pair is characterized by a different value of $C = C(d^*)$.

Making the (rather drastic) approximation $C(d^*) = C$, independent of d*, the expressions assume the form:

$$I_E = 1/C(t+p-1)$$

and $$I_f = 1/C(t+p-1)[\{C/(C+(d^*-1)^*T)+C/(C+(d^*-1)^*T)+\ldots+1\}+(t-p)H(t-p)]$$

And, for the ratio:

$$I_f/I_E = \{C/(C+(d^*-1)^*T)+C/(C+(d^*-1)^*T)+\ldots+1\}+(t-p)H(t-p)$$

Examples of calculated profiles are shown in FIG. 11A to 11D.

This trial function may be generalized in various ways, for example by introducing an exponent, $\beta \neq 1$, to represent the high temperature portion of the melting curve, by permitting $\delta T$ to depend on d, or generally by supplying explicit calculated or experimentally determined melting temperatures, and by evaluating the parameter $C=C(d^*)$ for each probe-target pair.

Preferably, to analyze experimental data obtained with a set of probes of known p, regression analysis would be used to obtain d* and hence t.

IV.2 Thermodynamic Weights: $w(d)=c\ w(d-1)$

In analogy to the classic "zipper" models developed to describe the helix-coil transition of a polypeptide chain and the condensation of a pair of nucleic acid strands into a duplex (Cantor & Schimmel, "Biophysical Chemistry", Vol 3, 1981), the partition function of the probe-target duplex repeat may be represented in the form $$Z = 1/(t+p-1)\Sigma_{(0<d<=d^*)} g_d \exp(-d\Delta F_0/kT)$$

where $\Delta F_0/kT$ represents the free energy of duplex formation per base pair which may be augmented by a nucleation term, $\sigma = \exp(-\Delta F_N/kT)$.

Setting $w_1 = w(d=1) = \exp(-\Delta F_0/kT) = c$, the expression assumes the form $$Z = 1/(t+p-1)\Sigma_{(0<d<=d^*)} g_d \sigma c^d$$

Neglecting the nucleation term, this leads to the geometric weight function $w(d)=c_d$ and the following expressions for the intensities:

$$I_E = c^{d^*}/t+p-1$$

and $$I_f = c^{d^*}\{(1-c^{d^*-1})/c^{d^*}(1-c)+(t-p)H(t-p)\}/t+p-1$$

and, for the ratio:

$$I_f/I_E = (1-c^{d^*-1})/c^{d^*}(1-c)+(t-p)H(t-p)$$

The nucleation term, $\sigma$, will reflect the increasing entropic penalty of forming a duplex of increasing length, as discussed herein. For example, the probability of forming the first duplex repeat between a probe and a target having t repeats within a sequence of total length L will be inversely proportional to the volume of the coil formed by the target in solution, $\sim 1/L^3$; that is, with $L \sim aN^\nu$, N denoting the total number of nucleotides in the sequence, the probability of initial pair formation will scale as $\sim(t/N)^{3\nu}$; $\sigma$ may be treated as an additional parameter for purposes of regression analysis of experimental data.

IV.3 Other Weight Functions

Two-State Model—A situation of interest to experiment occurs when two or more probes are provided to capture a given target at a set operating temperature, T; of the multiple partial and full duplex configurations, those with $d \leq d^\wedge$ duplex repeats are in the high temperature regime ($T_M(d \leq d^\wedge) < T$) while those with $d > d^\wedge$ duplex repeats are in the low temperature regime ($T < T_M(d > d^\wedge)$), $d^\wedge$ denoting the value of d indicating cross-over from low to high temperature. While the cross-over generally will reflect the shape of the duplex "melting" curve (Cantor & Smith, "Genomics"), a simple but instructive model results under the assumption of a melting curve with a step at $d=d^\wedge$ such that all (partial or full duplex) configurations with $d \leq d^\wedge$ are assigned a weight $w(d)=c_{Low}$ and all those with $d > d^\wedge$ are assigned a weight $w(d)=c_{High}$. Explicit expressions are obtained for the trial function in Examples IV.1, treating $d^\wedge$ and the ratio $c_{Low}/c_{High}$ as adjustable parameters.

Preferred Configurations: Modulations—More complex situations may be described by constructing appropriate weight functions, $w=w(d)$. An interesting situation arises when the pitch of 10 base pairs/turn of B DNA of random sequence is incommensurate with the preferred alignment of probe and target repeats, each repeat containing, say, four bases, such that repeat boundaries in probe and target strands are juxtaposed (see FIG. 2). In commensurate alignment for certain values of d may result in undertwisting or overtwisting of the helix formed by the probe-target complex, increasing the free energy, and hence reducing the probability of formation of the corresponding duplex states.

An example of this type would be the preference of configurations in which the product rd, r denoting the number of bases in the repeat, matches the pitch of the double helix, i.e., rd/10=n, n denoting an integer. For example, with r=4, duplex configurations with d=5, d=10, d=15, etc would display enhanced intensities relative to other duplex configurations, leading to modulations in intensity of profiles. A simple trial function, based on Example IV.1, would be $w(d)=c+(-1)^d \delta c$, producing "odd"-"even" modulations; more general functional forms also are possible. Modulated versions of the weight functions in Examples IV.2 and IV.3 also may be considered.

Loops—At high temperature, long probes, p>t, also can display loops (FIG. 9), permitting the probe to form two or more stretches of duplex with the target. While the probability of formation of a loop of d repeats, $\sim d^{-3/2}$, is lower than the probability of formation of a tail of d repeats, $\sim d^{-1/2}$, multiple such loops can form (and migrate along the target), a fact that reduces the probe's loss of configurational entropy. The method of the present invention is readily extended to include loop configurations by counting the number of such states (see e.g., Fleer et al, "Polymers at Interfaces", Chapt 4).

It should be understood that the terms, examples and expressions above are exemplary only, and not limiting, that steps in method claims can be performed in any order, unless otherwise specified, and that the scope of the invention is defined only in the claims which follow, and includes all equivalents of the subject matter of the claims.

What is claimed is:

1. A method for determining the number of tandem repeat units in a target oligonucleotide, comprising:
   selecting at least two probes, under the following selection criteria:
   (i) each probe has repeated sequence elements ("probe repeats"), each probe repeat being complementary to the target oligonucleotide's repeat unit ("target repeat"), but each probe having fewer probe repeats than the total number of target repeats present in the target oligonucleotide; and
   (ii) each probe, upon hybridizing to the target oligonucleotide under conditions permitting the formation of a duplex of at least one repeat unit, is labeled with a first color in configurations in which the probe's 3' end is aligned in juxtaposition to a target repeat nucleotide which is not the 5' terminal target repeat nucleotide, and labeled with a second, different color in the configuration in which the probe's 3' end is aligned in juxtaposition to the 5' terminal target repeat nucleotide;
   hybridizing said at least two probes to one target oligonucleotide, and determining, for each of said at least two probes the intensities of the respective signals of the first and second colors;
   analyzing the intensities of the signals resulting from the hybridization step where said intensities reflect the probability of different duplex configurations for probes and targets having respectively particular probe repeats and target repeats; and
   determining the number of tandem repeats in the target oligonucleotide by regression analysis.

2. The method of claim 1 wherein the probability for each possible duplex configuration is weighted such that for increasing reaction temperature, the formation of said duplex is less likely.

3. A method for determining the number of tandem repeat units in a target oligonucleotide, comprising:
   selecting at least one probe, under the following selection criteria:
   (i) the probe has a number (p) of tandem repeat sequences complementary to the target tandem repeat sequences, but has fewer tandem repeats than the total number (t) of tandem repeats present in the target oligonucleotide; and (ii) the probe, upon hybridizing to the target oligonucleotide to form a duplex of p repeat units, is labeled with a first color in configurations having the probe's 3' end aligned in juxtaposition to a target repeat nucleotide which is not the 5' terminal nucleotide, and labeled with a second, different color in the configuration having the probe's 3' end aligned in juxtapostion to the 5' terminal target repeat nucleotide;

hybridizing said probe to one target oligonucleotide under conditions ensuring the formation of a duplex of p (<t) repeats and determining for that probe the intensities of the respective signals of the first and second colors; and determining the length of the unknown target oligonucleotide using the formula:

when the number of repeated sequence elements in the probe is (p), and the number of repeated sequence elements in the target is (t), then the ratio of the intensity of the signal of the first color to the intensity of the signal of the second color associated with the probe, is proportional to t−p.

4. The method of claim 3, comprising the additional step of providing internal calibration by permitting a second probe of length p', differing in length from that of the first probe, p, to form a duplex of p' repeat units and determining for that probe the intensities of the respective signals of the first and second colors.

5. The method of claim 3 wherein an assay temperature is selected which is higher than the melting temperature of partial duplex configurations so as to favor formation exclusively of full lenath duplex configurations.

6. The method of claim 3, comprising the additional step of providing calibration of said intensity ratios by permitting the probe to form a duplex of p repeat units with a reference target comprising a known number of repeated sequence elements and determining for that probe the intensities of the respective signals of the first and second colors.

7. The method of claim 6 wherein the additional step is performed following the hybridization step of said probe to one target oligonucleotide.

8. The method of claims 1 or 3 used to determine the number of tandem repeat units in a plurality of target oligonucleotides, wherein the 5' ends of each of a group of probes with different numbers of tandem repeats are attached to an encoded particle, encoded such that the identity of the probe attached can be determined by decoding.

9. The method of claims 1 or 3 wherein the labeling step is performed by 3' extension of the probe by a single labeled ddNTP, wherein a first ddNTP, labeled with the first color, is complementary to the target nucleotide X in the 3' terminal position of the target repeat unit, and a second ddNTP, labeled with the second color, is complementary to the target nucleotide Y in the position immediately adjacent to the 5' terminus of the 5' terminal tandem repeat;

provided that X and Y are not the same.

10. The method of claim 1 or 3 wherein the labeling step is performed by 3' extension of the probe by a single labeled ddNTP, wherein a first ddNTP, labeled with the first color, is complementary to the target nucleotide A in the 3' terminal position of the target repeat unit, and a second ddNTP, labeled with the second color, is complementary to a target nucleotide B in a position in the region adjacent to the 5' end of the 5' terminal tandem repeat but not in the position immediately adjacent to the 5' end of the 5' terminal tandem repeat; provided that A and B are not the same.

11. The method of claims 1 or 3 wherein the first and last nucleotides in the probe's tandem repeats do not align with the first and last nucleotides in the target's tandem repeats, and wherein, upon hybridization of the probe to the 5' terminal repeat end of the target, the target nucteotide located immediately adjacent to the target nucleotide juxtaposed to the probe's 3' terminus is different from the nucleotide in the 3' terminal position of a target repeat unit.

12. The method of claims 1 or 3 used to simultaneously determine the number of tandem repeat units in a plurality of target oligonucleotides, wherein the 5' end of each of a group of selected probes differing in the number of probe repeats is attached to an encoded particle, encoded such that the identity of the probe attached can be determined by decoding.

13. In a method of determining the number of tandem repeat units in a target, identifying probes having a greater number of tandem repeat units than the number of tandem repeats in the target, comprising:

selecting a plurality of probes, under the following selection criteria:

(i) each probe has a series of tandem repeat sequences complementary to the target tandem repeat sequences, and some probes (p') have more tandem repeats than the total number of tandem repeats present in the target oligonucleotide; and (ii) upon hybridizing with a target oligonucleotide, where each probe's 3' end aligns with a target tandem repeat nucleotide which is not the 5' terminal tandem repeat target nucleotide, the probe is labeled with a first color, and where its 3' end aligns with a target tandem repeat nucleotide which is the 5' terminal target nucleotide, the probe is labeled with a second color;

providing an adapter oligonucleotide segment having two portions, a first of which is complementary to the flanking region adjacent to the 5' end of the target tandem repeat units and a second of which is complementary to a tandem repeat section of the probes, the second portion including at least one additional nucleotide which can align with a nucleotide added to the 3' end of the p' probes;

provided that said additional nucleotide is not the same as the nucleotide at the 3' end of a target repeat unit or the nucleotide at the 3' end of the target flanking sequence; and provided that a probe p' having its 3' end aligned with any part of the adapter is labeled with a third color;

hybridizing at least one said probe (which is not a p' probe) to at least one target oligonucleotide of known Length under conditions ensuring the formation of a duplex of p (<t) repeats, and determining the intensities of the respective signals from the first color and second colors;

hybridizing at least one said probe to at least one target oligonucleotide having an unknown number of repeat units, or to both an oligonucleotide and to a portion of the adapter sequence aligned with the 3' terminal repeat unit of the probe, said adapter being hybridized to said target oligonucleotide, under conditions ensuring the formation of a duplex of p ($\leq$t) repeats and determining the presence of the first color, and if there is any, the intensities of the respective signals from the first and second colors, and if there is no first color, determine the presence of any of the third color; but where the first color is present; and determining the length of the unknown target oligonucleotide using the formula:
when the number of repeat sequences in the probe is (p), and the number of repeat sequences in the target is (t), then the ratio of the intensity of the signal of the first color over the intensity of the signal of the second color is proportional to p−t.

14. The method of claim 13 used to simultaneously determine the number of tandem repeat units in a plurality of target oligonucleotides wherein the 5' ends of each of a group of probes with different numbers of tandem repeats are attached to an encoded particle, encoded such that the identity of the probe attached can be determined by decoding.

15. The method of claim 13 wherein the labeling is done by adding labeled ddNTPs to the 3' terminal end of the probe, wherein a first ddNTP nucleotide labeled with the first color is complementary to the nucleotide X, a second ddNTP nucleotide labeled with the second color different than the first color is complementary to a nucleotide Y, and a third ddNTP nucleotide labeled with the third color different is complementary to the nucleotide N.

16. The method of claim 13 wherein hybridizing steps are not done in a sequential manner.

17. A method for determining the number of tandem repeat units in a target oligonucleotide, comprising:
selecting a plurality of probes, under the following selection criteria:
(i) each probe has a series of tandem repeat sequences, p, complementary to the target tandem repeat sequences, t, and all probes have more tandem repeats than the total number of tandem repeats present in a target oligonucleotide; and
(ii) upon hybridizing with a target oligonucleotide, where each probe's 5' end aligns with a target tandem repeat nucleotide which is not the 3' terminal tandem repeat target nucleotide, the target is labeled with a first color, and where a probe's 5' end aligns with a target tandem repeat nucleotide which s the 3' terminal target nucleotlde, the target is labeled with a second different color;
hybridizing at least one said probe to at least one target oligonucleotide of known length under conditions ensuring the formation of a duplex of p (>t) repeats;
cleaving from the probe and target the un-annealed 3' terminal portions;
determining the intensities of the respective signals from the first and second colors;
hybridizing at least one said probe to at least one target oligonucleotide of unknown length;
cleaving from the probe and target the un-annealed 3' terminal portions;
determining the intensities of the respective signals from the first and second colors;
and
determining the length of the unknown target oligonucleotide using the formula:
the ratio of the intensity of the signal of the first color over the intensity of the signal of the second color associated with the same probe as that associated with the first color, is proportional to p−t.

18. The method of claim 17 used to simultaneously determine the number of tandem repeat units in a plurality of target oligonucleotides, wherein the 5' ends of each of a group of probes with different numbers of tandem repeats are attached to an encoded particle, encoded such that the identity of the probe attached can be determined by decoding.

19. The method of claim 17 wherein the labeling is done by adding labeled ddNTPs to the 3' terminal end of the probe, wherein a first ddNTP nucleotide labeled with the first color is complementary to the nucleotide at the 3' end of the probe terminal repeat unit, and a second ddNTP nucleotide labeled with the second color is complementary to a second nucleotide Y in the probe sequence immediately adjacent to the 5' end of the 5' terminal tandem repeat unit in the probe; provided that the first and second nucleotides are not the same.

20. The method of claim 17 wherein cleaving is done using exonuclease I.

* * * * *

UNITED STATES PATENT AND TRADEMARK OFFICE
CERTIFICATE OF CORRECTION

| | |
|---|---|
| PATENT NO. | : 7,202,038 B2 |
| APPLICATION NO. | : 10/913987 |
| DATED | : August 10, 2007 |
| INVENTOR(S) | : Michael Seul |

Page 1 of 1

It is certified that error appears in the above-identified patent and that said Letters Patent is hereby corrected as shown below:

Claim 5, column 21, line 34, change "lenath" to --length--.
Claim 13, column 22, line 52, change "Length" to --length--.
Claim 17, column 23, line 39, change "s" to --is--.
Claim 17, column 23, line 40, change "nucleotlde" to --nucleotide--.

Signed and Sealed this

Ninth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,202,038 B2
APPLICATION NO. : 10/913987
DATED : April 10, 2007
INVENTOR(S) : Michael Seul Page 1 of 1

It is certified that error appears in the above-identified patent and that said Letters Patent is hereby corrected as shown below:

Claim 5, column 21, line 34, change "lenath" to --length--.
Claim 13, column 22, line 52, change "Length" to --length--.
Claim 17, column 23, line 39, change "s" to --is--.
Claim 17, column 23, line 40, change "nucleotlde" to --nucleotide--.

This certificate supersedes the Certificate of Correction issued September 9, 2008.

Signed and Sealed this

Thirtieth Day of September, 2008

JON W. DUDAS
*Director of the United States Patent and Trademark Office*